US006255323B1

(12) United States Patent
Huang et al.

(10) Patent No.: US 6,255,323 B1
(45) Date of Patent: Jul. 3, 2001

(54) CYANOGUANIDINE COMPOUNDS

(75) Inventors: Tai-Nang Huang, Lexington; Guiqing Liang, Woburn, both of MA (US); Weimin Liu, Shelton, CT (US); Teresa Przewloka, Maynard, MA (US); Ming Shen, Guilford, CT (US); Shijie Zhang, N. Billerica, MA (US)

(73) Assignee: Shionogi Bioresearch Corp., Lexington, MA (US)

( * ) Notice: Subject to any disclaimer, the term of this patent is extended or adjusted under 35 U.S.C. 154(b) by 0 days.

(21) Appl. No.: 09/545,430

(22) Filed: Apr. 7, 2000

Related U.S. Application Data

(60) Provisional application No. 60/128,665, filed on Apr. 9, 1999, provisional application No. 60/148,429, filed on Aug. 11, 1999, and provisional application No. 60/151,808, filed on Aug. 31, 1999.

(51) Int. Cl.[7] ............ C07D 213/75; C07D 215/38; A61K 31/44; A61K 31/47
(52) U.S. Cl. ............ 514/313; 546/163; 546/306; 514/353
(58) Field of Search ............ 546/163, 306; 514/313, 353

(56) References Cited

U.S. PATENT DOCUMENTS

| 5,264,445 | 11/1993 | Robertson et al. | 514/353 |
|---|---|---|---|
| 5,563,160 | 10/1996 | Bramm et al. | 514/353 |
| 5,668,157 | 9/1997 | Humphrey et al. | 514/353 |
| 5,696,140 | 12/1997 | Bramm et al. | 514/353 |

FOREIGN PATENT DOCUMENTS

| 1 489 879 | 10/1977 | (GB) . |
|---|---|---|
| WO 98/54145 | 12/1998 | (GB) . |
| WO 94/06770 | 3/1994 | (WO) . |
| WO 98/54141 | 12/1998 | (WO) . |
| WO 98/54142 | 12/1998 | (WO) . |
| WO 98/54143 | 12/1998 | (WO) . |
| WO 98/54144 | 12/1998 | (WO) . |
| WO 98/54146 | 12/1998 | (WO) . |

OTHER PUBLICATIONS

"Synthesis and Hypotensive Activity of N–Alkyl–N"–cyano–N'–pyridylguanidines," Petersen et al. Journal of Medicinal Chemistry, vol. 21, No. 8, Aug. 1978, pp 773–781.

"Novel Cyanoguanidines With Potent Oral Antitumor Activity," Schou et al., Bioorganic & Medicinal Chemistry Letters, vol. 7, No. 24, 1997, pp 3095–3100.

The Proceedings of the 90th American Association for Cancer Research Annual Meeting, Research Annual Meeting, Apr. 10–14, 1999, Abstract # 1984.

The Proceedings of the 90th American Association for Cancer Research Annual Meeting, Research Annual Meeting, Apr. 10–14, 1999, Abstract # 1985.

The Proceedings of the 90th American Association for Cancer Research Annual Meeting, Research Annual Meeting, Apr. 10–14, 1999, Abstract # 1986.

The Proceedings of the 90th American Association for Cancer Research Annual Meeting, Research Annual Meeting, Apr. 10–14, 1999, Abstract # 7.

The Proceedings of the 90th American Association for Cancer Research Annual Meeting, Research Annual Meeting, Apr. 10–14, 1999, Abstract # 5.

*Primary Examiner*—Zinna Northington Davis
(74) *Attorney, Agent, or Firm*—Fish & Richardson P.C.

(57) ABSTRACT

A cyanoguanidine compound of the following formula:

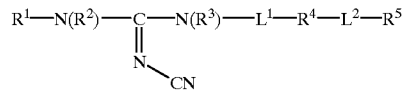

is disclosed. A cyanoguanidine compound of the present invention possess a high specificity for tumor cells. Also disclosed are methods for preparing a cyanoguanidine compound.

39 Claims, No Drawings

CYANOGUANIDINE COMPOUNDS

CROSS REFERENCE TO RELATED APPLICATIONS

Pursuant to 35 USC §119(e), this application claims the benefit of prior U.S. provisional applications 60/128,665, filed Apr. 9, 1999; 60/148,429, filed Aug. 11, 1999; and 60/151,808, filed Aug. 31, 1999.

BACKGROUND

Cancer remains a formidable disease with a high mortality rate in today's society. Indeed, cancer is second only to cardiovascular disease as a cause of death, killing one out of four people in developed countries.

Cancerous tumors commonly originate from normal cells which transform into malignant cells or tumors. The initial tumor growth may be slow and thus may be difficult to detect. The growth often becomes more aggressive and invasive with time, eventually spreading throughout the whole body and resulting in death.

Cancer treatment usually includes immunotherapy, surgery, radiation, hormones, and chemotherapy. In the past forty years, cancer chemotherapy has truly revolutionized the treatment of malignant tumors. Curative treatment has been discovered for many of the cancers that affect children and young adults, including acute lymphocytic leukemia, Hodgkin's disease, testicular carcinoma, and many others. However, despite being a powerful method of treating cancer, chemotherapy does suffer from a few problems. The most prominent problem is the low specificity of the anti-cancer agents. That is, most anticancer agents do not adequately distinguish normal cells from cancer cells. As a result, they often carry undesirable serious side effects. Such limitations of conventional chemotherapies underscore the urgent need for new anticancer agents with high antitumor activities and specificity to the cancerous cells.

SUMMARY

An aspect of this invention relates to compounds of formula (I):

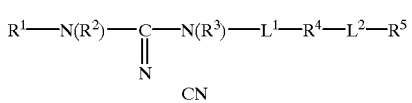

$R^1$ is 3-pyridyl, 4-pyridyl, or quinolinyl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, alkylcarbonyloxy, alkyloxycarbonyl, alkylcarbonyl, alkylcarbonylamino, aminocarbonyl, alkylsulfonylamino, aminosulfonyl, sulfonic acid, or alkylsulfonyl. Each of $R^2$ and $R^3$, independently, is hydrogen, alkyl, alkoxy, hydroxylalkyl, thioalkyl, aminoalkyl, cycloalkyl, heterocycloalkyl, aryl, heteroaryl, alkylcarbonyloxy, alkyloxycarbonyl, alkylcarbonyl, alkylcarbonylamino, or aminocarbonyl. $L^1$ is $—X^1—Y^1—X^2—$. Each of $X^1$ and $X^2$, independently, is a bond, or a $C_{1-6}$ alkylene chain optionally containing a double bond or a triple bond and further optionally substituted with alkoxy, hydroxyl, halo, carboxyl, amino, nitro, cyano, cycloalkyl, heterocycloalkyl, aryl, heteroaryl, aminosulfonyl, alkylsulfonylamino, alkylcarbonyloxy, alkyloxycarbonyl, alkylcarbonyl, formyl, alkylcarbonylamino, or aminocarbonyl. $Y^1$ is —O—, —S—, —SO—, —SO$_2$—, —N($R^a$)—, —CO—, —N($R^a$)—CO—, —CO—N($R^a$)—, —N($R^a$)—CO—CO—, —N($R^a$)—SO$_2$—, —SO$_2$—N($R^a$)—, —N($R^a$)—CO—O—, —O—CO—N($R^a$)—, —N($R^a$)—CO—N($R^b$)—, —N($R^a$)—CS—N($R^b$)—CO—, —CO—, —CO—N($R^a$)—CS—N($R^b$)—, —O—CO—, —CO—O—, —O—SO$_2$—, —SO$_2$—O—, —O—S—CO—N($R^a$)—, —N($R^a$)—CO—S—O—, —O—CO—O—, —CO—N($R^a$)—S—CO—N($R^b$)—, —N($R^a$)—CO—S—N($R^b$)—CO—, or a bond. Each of $R^a$ and $R^b$, independently, is hydrogen, alkyl, alkoxy, hydroxylalkyl, hydroxyl, amino, nitro, cyano, halo, haloalkyl, cycloalkyl, heterocycloalkyl, aryl, heteroaryl, aralkyl, or heteroaralkyl. $R^4$ is aryl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, nitro, cyano, aryloxy, heteroaryloxy, aralkyloxy, heteroaralkyloxy, alkylcarbonyloxy, alkyloxycarbonyl, alkylcarbonyl, formyl, oxo, alkylcarbonylamino, aminocarbonyl, alkylsulfonylamino, aminosulfonyl, sulfonic acid, or alkylsulfonyl. $L_2$ is $—X^3—Y^2—X^4—$ in which each of $X^3$ and $X^4$, independently, is a bond, or a $C_{1-6}$ alkylene chain optionally containing a double bond or a triple bond and further optionally substituted with alkoxy, hydroxyl, halo, carboxyl, amino, nitro, cyano, cycloalkyl, heterocycloalkyl, aryl, heteroaryl, aminosulfonyl, alkylsulfonylamino, alkylcarbonyloxy, alkyloxycarbonyl, alkylcarbonyl, formyl, alkylcarbonylamino, or aminocarbonyl. $Y^2$ is —O—, —S—, —SO—, —SO$_2$—, —N($R^c$)—, —CO—, —N($R^c$)—CO—, —CO—N($R^c$)—, —N($R^c$)—CO—CO—, —N($R^c$)—SO$_2$—, —SO$_2$—N($R^c$)—, —N($R^c$)—CO—O—, —O—CO—N($R^c$)—, —N($R^c$)—CO—N($R^d$)—, —N($R^c$)—CS—N($R^d$)—CO—, —CO—N($R^c$)—CS—N($R^d$)—, —O—CO—, —CO—O—, —O—SO$_2$—, —SO$_2$—O—, —O—S—CO—N($R^c$)—, —N($R^c$)—CO—S—O—, —O—CO—O—, —CO—N($R^c$)—S—CO—N($R^d$)—, —N($R^c$)—CO—S—N($R^d$)—CO—, or a bond. Each of $R^c$ and $R^d$, independently, is hydrogen, alkyl, alkoxy, hydroxylalkyl, hydroxyl, amino, nitro, cyano, halo, haloalkyl, cycloalkyl, heterocycloalkyl, aryl, heteroaryl, aralkyl, or heteroaralkyl. $R^5$ is cycloalkyl, heterocycloalkyl, cycloalkenyl, heterocycloalkenyl, aryl, or heteroaryl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, nitro, cyano, aryloxy, heteroaryloxy, aralkoxy, heteroaralkoxy, alkylcarbonyloxy, alkyloxycarbonyl, arylcarbonyloxyalkyl aryloxycarbonylalkyl, alkylcarbonyl, formyl, oxo, aminocarbonyl, alkylcarbonylamino, alkylsulfonylamino, aminosulfonyl, aminocarbonyloxy, or alkyloxycarbonylamino. Note that each of $Y^1$ and $Y^2$ is not a bond simultaneously, and that when neither $Y^1$ nor $Y^2$ is a bond, at least one of $X^2$, $R^4$, and $X^3$ is not a bond.

Another aspect of this invention relates to cyanoguanidine compounds having the formula (I) as depicted above. $R^1$ is 3-pyridyl, 4-pyridyl, or quinolinyl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, alkylcarbonyloxy, alkyloxycarbonyl, alkylcarbonyl, alkylcarbonylamino, aminocarbonyl, alkylsulfonylamino, aminosulfonyl, sulfonic acid, or alkylsulfonyl. Each of $R^2$ and $R^3$, independently, is hydrogen, alkyl, alkoxy, hydroxylalkyl, thioalkyl, aminoalkyl, cycloalkyl, heterocycloalkyl, aryl, heteroaryl, alkylcarbonyloxy, alkyloxycarbonyl, alkylcarbonyl, alkylcarbonylamino, or aminocarbonyl. $L^1$ is —$X^1$—$Y^1$—$X^2$—. Each of $X^1$ and $X^2$, independently, is a bond, or a $C_{1-6}$ alkylene chain optionally containing a double bond or a triple bond and further optionally substituted with alkyl, alkenyl, alkynyl, alkoxy, hydroxyl, halo, carboxyl, amino, nitro, cyano, cycloalkyl, heterocycloalkyl, aryl, heteroaryl, aminosulfonyl, alkylsulfonylamino, alkylcarbonyloxy, alkyloxycarbonyl, alkylcarbonyl, formyl, alkylcarbonylamino, or aminocarbonyl. $Y^1$ is —O—, —S—, —SO—, —$SO_2$—, —$N(R^a)$—, —CO—, —$N(R^a)$—CO—, —CO—$N(R^a)$—, —$N(R^a)$—CO—CO—, —$N(R^a)$—$SO_2$—, —$SO_2$—$N(R^a)$—, —$N(R^a)$—CO—O—, —O—CO—$N(R^a)$—, —$N(R^a)$—CO—$N(R^b)$—, —$N(R^a)$—CS—$N(R^b)$—CO—, —CO—N($R^a$)—CS—$N(R^b)$—, —O—CO—, —CO—O—, —O—$SO_2$—, —$SO_2$—O—, —O—S—CO—$N(R^a)$—, —$N(R^a)$—CO—S—O—, —O—CO—O—, —CO—N($R^a$)—S—CO—$N(R^b)$—, N($R^a$)—CO—S—$N(R^b)$—CO—, or a bond. Each of $R^a$ and $R^b$, independently, is hydrogen, alkyl, alkoxy, hydroxylalkyl, hydroxyl, amino, nitro, cyano, halo, haloalkyl, cycloalkyl, heterocycloalkyl, aryl, heteroaryl, aralkyl, or heteroaralkyl. $R^4$ is a bond, or cycloalkyl, cycloalkenyl, or aryl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, nitro, cyano, aryloxy, heteroaryloxy, aralkyloxy, heteroaralkyloxy, alkylcarbonyloxy, alkyloxycarbonyl, alkylcarbonyl, formyl, oxo, alkylcarbonylamino, aminocarbonyl, alkylsulfonylamino, aminosulfonyl, sulfonic acid, or alkylsulfonyl. $L^2$ is —$X^3$—$Y^2$—$X^4$—. Each of $X^3$ and $X^4$, independently, is a bond, or a $C_{1-6}$ alkylene chain optionally containing a double bond or a triple bond and further optionally substituted with alkyl, alkenyl, alkynyl, alkoxy, hydroxyl, halo, carboxyl, amino, nitro, cyano, cycloalkyl, heterocycloalkyl, aryl, heteroaryl, aminosulfonyl, alkylsulfonylamino, alkylcarbonyloxy, alkyloxycarbonyl, alkylcarbonyl, formyl, alkylcarbonylamino, or aminocarbonyl; and $Y^2$ is —O—, —S—, —SO—, —$SO_2$—, —$N(R^c)$—, —CO—, —$N(R^c)$—CO—, —CO—$N(R^c)$—, —$N(R^c)$—CO—CO—, —$N(R^c)$—$SO_2$—, —$SO_2$—N($R^c$)—, —$N(R^c)$—CO—O—, —O—CO—$N(R^c)$—, —$N(R^c)$—CO—$N(R^d)$—, —$N(R^c)$—CS—$N(R^d)$—CO—, —CO—$N(R^c)$CS—$N(R^d)$—, —O—CO—, —CO—O—, —O—$SO_2$—, —$SO_2$—O—, —O—S—CO—$N(R^c)$—, —$N(R^c)$—CO—S—O—, —O—CO—O—, —CO—N($R^c$)—S—CO—$N(R^d)$—, —$N(R^c)$—CO—S—$N(R^d)$—CO—, or a bond. Each of $R^c$ and $R^d$, independently, is hydrogen, alkyl, alkoxy, hydroxylalkyl, hydroxyl, amino, nitro, cyano, halo, haloalkyl, cycloalkyl, heterocycloalkyl, aryl, heteroaryl, aralkyl, or heteroaralkyl. $R^5$ is a cyclic moiety having 12–20 ring atoms, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, nitro, cyano, aryloxy, heteroaryloxy, aralkoxy, heteroaralkoxy, alkylcarbonyloxy, alkyloxycarbonyl, arylcarbonyloxyalkyl, aryloxycarbonylalkyl, alkylcarbonyl, formyl, oxo, aminocarbonyl, alkylcarbonylamino, alkylsulfonylamino, aminosulfonyl, aminocarbonyloxy, or alkyloxycarbonylamino. When neither one of $Y^1$ and $Y^2$ is a bond, at least one of $X^2$, $R^4$, and $X^3$ is not a bond.

Set forth below are some examples of a cyanoguanidine compounds of this invention: 5-dimethylaminonaphthalene-1-sulfonic acid (4-(N'-cyano-N"-pyridin-4-yl-guanidinomethyl)-phenyl)-amide, naphthalene-1-sulfonic acid (4-(N'-cyano-N"-pyridin-4-yl-guanidinomethyl)-phenyl)-amide, N-(4-(N'-cyano-N"-pyridin-4-yl-guanidinomethyl)-phenyl)-3-trifluoromethyl-benzenesulfonamide, 2,4,6-trimethyl-N-(4-(N'-cyano-N"-pyridin-4-yl-guanidinomethyl)-phenyl)-benzenesulfonamide, 4-chloro-N-(4-(N'-cyano-N"-pyridin-4-yl-guanidinomethyl)-phenyl)-benzenesulfonamide, N-{2-[2-( 10,11-dihydro-5H-dibenzo[a,d]cyclohepten-5-yloxy)-ethoxy]-ethyl}-N'-cyano-N"-pyridin-4-yl-guanidine, and N-[2-(10,11-dihydro-5H-dibenzo[a,d]cyclohepten-5-yloxy)-ethyl]-N-[2-(N'-cyano-N"-pyridin-4-yl-guanidino)-ethyl]-acetamide.

Note that two adjacent substituents on the pyridine ring can join together to form a 4- to 7-membered cyclic moiety together with the two carbon atoms to which the substituents are bonded. The cyclic moiety can be cycloalkyl, heterocycloalkyl, cycloalkenyl, heterocycloalkenyl, aryl, or heteroaryl. For example, a quinolinyl is formed when the cyclic moiety is a benzene. Heteroatoms such as nitrogen, oxygen, and sulfur can be included in the cyclic moiety.

An N-oxide derivative or a salt of each of the cyanoguanidine compounds described above is also within the scope of this invention. For example, the nitrogen ring atom of the pyridine ring can form an oxide in the presence of a suitable oxidizing agent such as m-chloroperbenzoic acid or $H_2O_2$. A pharmaceutically acceptable salt can be formed when a cyanoguanidine compound of this invention reacts with an inorganic or organic acid. Some examples of such an acid include hydrochloric acid, hydrobromic acid, hydroiodic acid, sulfuric acid, phosphoric acid, p-bromophenylsulfonic acid, carbonic acid, succinic acid, citric acid, benzoic acid, and acetic acid. Examples of pharmaceutically acceptable salts thus formed include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, and maleate.

It should be recognized that a cyanoguanidine compound of this invention may contain chiral carbon atoms. In other words, it may have optical isomers or diastereoisomers. These isomers are all within the scope of this invention.

As used herein, alkyl is a straight or branched hydrocarbon chain containing 1 to 12 carbon atoms. Examples of alkyl include, but are not limited to, methyl, ethyl, propyl, isopropyl, butyl, isobutyl, sec-butyl, tert-butyl, n-pentyl, 2-methylhexyl, 3-ethyloctyl, and 4-ethyldecyl.

The terms "alkenyl" and "alkynyl" refer to a straight or branched hydrocarbon chain containing 2 to 12 carbon atoms and one or more (e.g., 1–6) double or triple bonds, respectively. Some examples of alkenyl and alkynyl are allyl, 2-butenyl, 2-pentenyl, 2-hexenyl, 2-butynyl, 2-pentynyl and 2-hexynyl.

As used herein, a $C_{1-6}$ alkylene chain is a divalent hydrocarbon chain containing 1–6 carbon atoms. For example, a $C_1$ alkylene chain and a $C_2$ alkylene chain refer to a methylene and an ethylene group, respectively.

By cycloalkyl is meant a cyclic alkyl group containing 3 to 8 carbon atoms. Some examples of cycloalkyl are cyclopropyl, cyclopentyl, cyclohexyl, cycloheptyl, adamantyl, and norbornyl. Heterocycloalkyl is a cycloalkyl group containing 1–3 heteroatoms such as nitrogen, oxygen, or sulfur. Examples of heterocycloalkyl include piperidinyl, piperazinyl, tetrahydropyranyl, tetrahydrofuryl, and morpholinyl. Cycloalkenyl is a cycloalkyl group containing one or more (e.g., 1–3) double bonds. Examples of such a group include cyclopentenyl, 1,4-cyclohexa-di-enyl, cycloheptenyl, and cyclooctenyl groups. By the same token, heterocycloalkenyl is a heterocycloalkyl group containing one or more double bonds.

As used herein, aryl is an aromatic group containing 6–12 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1–3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

As used herein, a cyclic moiety is cycloalkyl, heterocycloalkyl, cycloalkenyl, heterocycloalkenyl, aryl, or heteroaryl. A cyclic moiety can also be fused rings and can be formed from two or more of the just-mentioned groups. Examples of a cyclic moiety having fused rings include fluorenyl, dihydro-dibenzoazepine, dibenzocycloheptenyl, 7H-pyrazino[2,3-c]carbazole, or 9,10-dihydro-9,10-[2] buteno-anthracene.

Each of the cycloalkyl, heterocycloalkyl, cycloalkenyl, heterocycloalkenyl, aryl, or heteroaryl described herein is optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, nitro, cyano, aryloxy, heteroaryloxy, aralkoxy, heteroaralkoxy, alkylcarbonyloxy, alkyloxycarbonyl, arylcarbonyloxyalkyl, aryloxycarbonylalkyl, alkylcarbonyl, formyl, oxo, aminocarbonyl, alkylcarbonylamino, alkylsulfonylamino, aminosulfonyl, aminocarbonyloxy, or alkyloxycarbonylamino.

Note that an amino group can be unsubstituted, mono-substituted, or di-substituted. It can be substituted with groups such as alkyl, cycloalkyl, heterocycloalkyl, aryl, heteroaryl, aralkyl, or heteroaralkyl. Halo refers to fluoro, chloro, bromo, or iodo.

Cyanoguanidine compounds of this invention possess an unexpectedly high specificity for tumor cells. Other features or advantages of the present invention will be apparent from the following detailed description of several embodiments, and also from the appending claims.

DETAILED DESCRIPTION

A cyanoguanidine compound of this invention can be prepared by a number of methods. Two methods (1) and (2) are described herein. Each of them employs a common starting material, S-methyl-N-cyano-N'-pyridylisothiourea or compound (A) as shown in the two schemes below. For preparation of this starting material, see Schou et al., Bioorganic & Medicinal Chemistry Letters, 7(24), 3095–3100 (1997).

In the synthetic scheme of method (1), the definitions of $R^1$, $R^2$, $R^3$, $R^4$, $R^5$, $X^1$, $X^2$, $X^3$, $X^4$, $Y^1$, and $Y^2$ have been provided above. Compound (A) is first coupled with a primary amine or secondary amine, $NH(R^3)$—$X^1$—$Y^{1'}$, to yield an intermediate, compound (B), which is then coupled with $X^{2'}$—$R^4$—$X^3$—$Y^{2'}$—$X^4$—$R^5$ to yield the desired cyanoguanidine compound. Examples of secondary amines include cyclic amines such as piperidinyl or piperazinyl. Note that $Y^{1'}$ and $X^{2'}$ are functionalities which, upon reacting with each other, yield moieties of $Y^1$ and $X^2$, respectively. For example, if the desired yl moiety is an amide, it can be formed by reacting an amine group ($Y^{1'}$) with a carboxyl group ($X^{2'}$) in the presence of a common coupling reagent such as benzotriazol-1-yloxytris(dimethylamino)-phosphonium hexafluorophosphate (BOP) or O-benzotriazol-1-yl-N,N,N,N'-tetramethyluronium hexafluorophosphate (HBTU). The following scheme also includes exemplary conditions in which five other $Y^1$ moieties, i.e., sulfonamide, urea, oxygen, amino, and sulfur linkages, are formed.

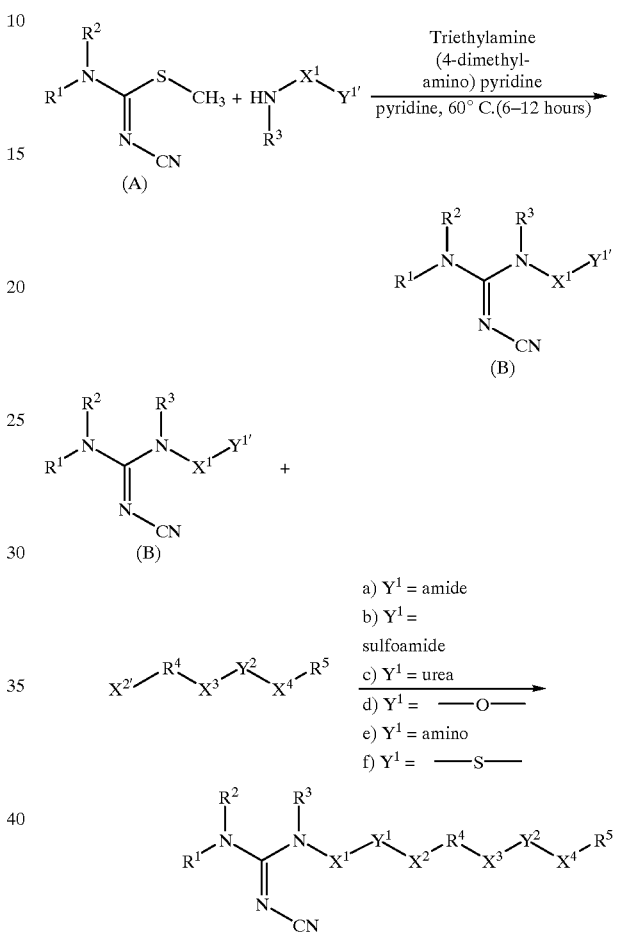

Method (1)

a) Diisopropylethylamine, benzotriazol-1-yloxy-tris(dimethylamino) phosphonium, dimethylformamide, room temperature
b) Pyridine, room temperature
c) Triethylamine, dimethylformamide, tetrahydrofuran, room temperature
d) Triphethylamine, diethylazodicarboxylate, tetrahydrofuran, room temperature
e) Sodium triacetoxyborohydride, glacial acetic acid, tetrahydrofuran, room temperature
f) Sodium hydroxide, Aliquat 336, tetrahydrofuran, room temperature Alternatively, compound (A) can be first coupled with $NH(R^3)$—$X^1$—$Y$ —$X^2$—$R^4$—$X^3$—$Y^{2'}$ to form an intermediate, which then reacts with $X^{4'}$—$R^5$ to form a cyanoguanidine compound of this invention. Similar to $Y^{1'}$ and $X^{2'}$, $Y^{2'}$ and $X^{4'}$ are functionalities, upon reacting with each other, yield moieties of $Y^2$ and $X^4$, respectively.

The scheme below shows yet another method of preparing a cyanoguanidine compound of this invention. According to this scheme, $NH(R^3)$—$X^1$—$Y^{1'}$ first reacts with $X^{2'}$—$R^4$—$X^3$—$Y^2$—$X^4$—$R^5$ to form an intermediate $NH(R^3)$ —$X^1$—$Y^1$—$X^2$—$R^4$—$X^3Y^2$—$X_3Y^2$—$X^4$—$R^5$, which, in turn, is coupled with compound (A) to form a cyanoguanidine compound of this invention.

Method (2)

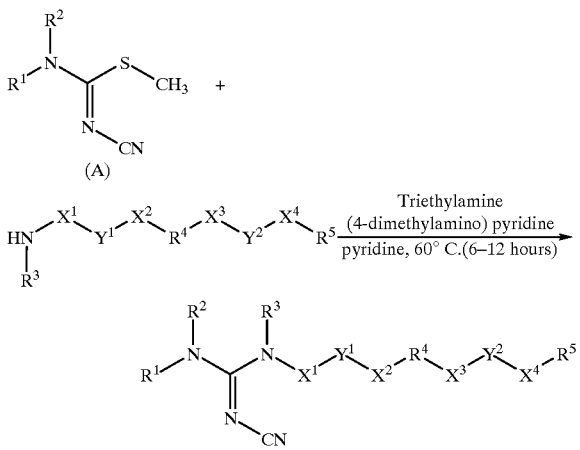

Compounds of formula (I) in which $R^4$ is a nitrogen-containing cyclic moiety, e.g., piperidinyl or imidazolyl, can be prepared by reacting $NH(R^3)-X^1-Y^1-X^2-R^4$ with $X^{3'}-Y^2-X^4-R^5$ to form an intermediate $NH(R^3)-X^1-Y^1-X^2-R^4-X^3-Y^2-X^4-R^5$ before further reacting with S-methyl-N-cyano-N'-pyridylisothio-urea or compound (A). See, e.g., Examples 7 and 8. The following scheme illustrates yet another method to prepare the intermediate $NH(R^3)-X^1-Y^1-X^2R^4-X^3-Y^2-X^4-R^5$ where $R^4$ is 2,4-imidazolyl:

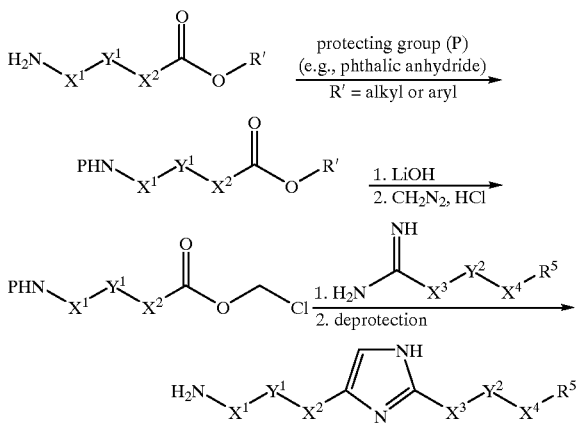

Note that appropriate protecting groups may be needed to avoid forming side products during the preparation of a cyanoguanidine compound. For example, the amino group of $NH(R^3)-X^1-Y^1$ can be first protected by a suitable amino protecting group such as trifluoroacetyl or tert-butoxycarbonyl prior to coupling with $X^{2'}-R^4-X^3-Y^2-X^4-R^5$. See, e.g., T. W. Greene, "Protective Groups in Organic Synthesis," John Wiley & Sons, Inc., New York (1981), for other suitable protecting groups.

A cyanoguanidine compound produced by the methods shown above can be purified by flash column chromatography, preparative high performance liquid chromatography, or crystallization.

A pharmaceutical composition containing an effective amount of one or more cyanoguanidine compounds of this invention is also within the scope of this invention. Some examples of tumors which can be treated by this pharmaceutical composition are leukemia, lung cancer, colon cancer, CNS cancer, melanoma, ovarian cancer, cervical cancer, renal cancer, prostate cancer, and breast cancer. The use of such a cyanoguanidine compound for the manufacture of a medicament for treating the above-mentioned tumors is also within the scope of this invention. Still another aspect of this invention is a method of treating tumor by administering to a patient a pharmaceutical composition containing an effective amount of a cyanoguanidine compound of this invention or its N-oxide derivative or salt. An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep. 1966, 50,219. Body surface area may be approximately determined from height and weight of the patient. See, e.g., Scientific Tables, Geigy Pharmaceuticals, Ardley, New York, 1970, 537. An effective amount of a cyanoguanidine compound of this invention can range from about 1 mg/kg to about 150 mg/kg. Effective doses will also vary, as recognized by those skilled in the art, dependant on route of administration, excipient usage, and the possibility of co-usage with other therapeutic treatments including use of other antitumor agents and radiation therapy.

The pharmaceutical composition may be administered via the parenteral route, including orally, topically, subcutaneously, intraperitoneally, intramuscularly, and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

A cyanoguanidine compound of this invention can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a cyanoguanidine compound with a solid carrier and a lubricant. Examples of solid carriers include starch and sugar bentonite. The cyanoguanidine compound can also be administered in a form of a hard shell tablet or a capsule containing a binder, e.g., lactose or mannitol, a conventional filler, and a tableting agent.

The antitumor activity of a cyanoguanidine compound of this invention can be evaluated by MTS colorimetric assay (see Example 149 below). Results obtained by using cell lines of various types of tumors are compared with those obtained by using cell lines of normal cells in this assay. Viability of the cells in each cell line is estimated by measuring the cellular conversion of a tetrazolium salt after incubating the cells in a solution containing a test cyanoguanidine compound in a 96 well plate. $IC_{50}$ values obtained by using an identical test compound on normal cells and cells of a particular tumor cell line are compared and their ratio ($IC_{50\ normal\ cell}/IC_{50\ cancer\ cell}$) indicates the cancer selectivity of that test compound. The higher the ratio, the higher the selectivity of the test compound towards that particular type of cancer cell.

The antitumor activity of a cyanoguanidine compound of this invention can also be evaluated by in vivo testing, e.g., human tumor xenograft regression assays. Animals bearing established tumors are treated with a test compound for a three-week period. The growth of the tumors and the general health of the animal are monitored during the three-week treatment and for two more weeks after treatment to determine if tumor regrowth occurs. See Example 150 below.

The toxicity of a cyanoguanidine compound of this invention is evaluated by preliminary sub-acute toxicity study and acute toxicity study. See Examples 151 and 152 below.

The following specific examples, which describe syntheses and biological testings of cyanoguanidine compounds of this invention, are to be construed as merely illustrative, and not limitative of the remainder of the disclosure in any way whatsoever.

In the following examples, the cyanoguanidine compounds were purified by using Gilson® preparative high performance liquid chromatography, equipped with a 306 pump and a WATERS BONDAPACK C18 column, eluted with methanol/water or acetonitrile/water. $^1$H Nuclear magnetic resonance spectra were recorded on a Varian Mercury 300 MHz spectrometer. ES mass spectra were recorded on a Finnigan Navigator mass spectrometer.

Without further elaboration, it is believed that one skilled in the art can, based on the description herein, utilize the present invention to its fullest extent. The following specific examples, which described syntheses, screening, and biological testing of various compounds of this invention, are therefore, to be construed as merely illustrative, and not limitative of the remainder of the disclosure in any way whatsoever. All publications recited herein, including patents, are hereby incorporated by reference in their entirety.

EXAMPLE 1

9H-fluorene-9-carboxylic acid (4-(N'-cyano-N"-pyridin-4-yl-guanidinomethyl)-phenyl)-amide (SBR-11-2727) was synthesized as follows In a reaction flask under nitrogen with magnetic stirring 1-cyano-2-methyl-3-pyridin-4-yl-isothiourea (0.35 g, 1.82 mmol) and 4-aminobenzylamine (0.25 g 2.05 mmol) were suspended in ethanol (1.5 mL). Triethylamine (0.19 g, 1.36 mmol) was added followed by (4-dimethylamino)pyridine (6 mg, 0.05 mmol). This reaction mixture was heated at 60° C. for 4 hours then cooled to room temperature. The resulting solid was collected by filtration and washed with cold ethanol (10 mL) to give N-(4-amino-benzyl)-N'-cyano-N"-quinolin-5-yl-guanidine as a white solid in 77% yield. $^1$H NMR (DMSO-$d_6$, ppm): 9.43 (s, 1H), 8.38 (d, 2H), 8.14 (s, 1H), 7.19 (d, 2H), 7.00 (d, 2H), 6.54 (d, 2H), 5.07 (s, 2H), 4.03 (d, 2H) ESMS 289.0 (M+23).

N-(4-Amino-benzyl)-N'-cyano-N"-quinolin-5-yl-guanidine (133 mg, 0.50 mmol) and 9H-fluorene-9-carboxylic acid (105 mg, 0.50 mmol) were suspended in N,N-dimethylformamide(1.0 mL). Benzotriazol-1-yloxy-tris(dimethylamino)phosphonium hexafluorophosphate (232 mg, 0.52 mmol) was added followed by N,N-diisopropylethylamine (0.20 mL, 1.15 mmol). The reaction mixture was stirred at room temperature for 24 hours and then diluted with ethyl acetate (30 mL). This solution was washed with water (30 mL×2) and dried over anhydrous sodium sulfate. The solvent was removed in vacuo to give the desired product (102 mg, 44.5%). $^1$H NMR (DMSO-$d_6$, ppm): 10.72 (s, 1H), 9.59 (bs, 1H), 8.37 (d, 2H), 8.27 (bs, 1H), 7.90 (d, 2H), 7.60 (t, 4H), 7.43 (t, 2H), 7.31 (m, 4H), 7.18 (m, 2H), 5.03 (s, 1H), 4.43 (d, 2H).

EXAMPLE 2

4-Chloro-N-(4-(N'-cyano-N"-quinolin-5-yl-guanidinomethyl)-phenyl)-benzenesulfonamide (SBR-11-3210) was synthesized as follows N-(4-Amino-benzyl)-N'-cyano-N"-quinolin-5-yl-guanidine (50 mg, 0.16 mmol) and 4-chloro-benzenesulfonyl chloride (41 mg, 0.19 mmol) were added to pyridine (1 mL). An exothermic reaction occurred and the suspension became homogeneous. This solution was shaken at room temperature for 12 hours. The reaction mixture was then diluted with ethyl acetate (8 mL) and washed with water (5 mL×3). The organic phase was dried over anhydrous sodium sulfate. The solvent was removed in vacuo and the residue was triturated with diethyl ether to give a solid product in 76% yield. $^1$H NMR (DMSO-$d_6$, ppm): 10.37 (s, 1H), 9.39 (s, 1H), 8.96 (m, 1H), 8.12 (m, 1H), 8.02 (d, 1H), 7.69 (m, 3H), 7.63 (d, 2H), 7.49 (m, 2H), 7.39 (m, 1H), 7.08 (m, 4H), 4.21 (d, 2H).

EXAMPLE 3

5-Dimethylamino-naphthalene-1-sulfonic acid (4-(N'-cyano-N"-pyridin-4-yl-guanidinomethyl)-phenyl)-amide (SBR-11-2897) was synthesized as follows N-(4-Amino-benzyl)-N'-cyano-N"-quinolin-5-yl-guanidine (400 mg, 1.50 mmol) and dansyl chloride (405 mg, 1.50 mmol) were combined in pyridine (15 mL). An exothermic reaction occurred and the suspension became homogeneous. This solution was shaken at room temperature for 12 hours. The reaction mixture was then diluted with ethyl acetate (80 mL) and washed with water (40 mL×3). The organic phase was dried over anhydrous sodium sulfate. The solvent was removed in vacuo to give a solid product which was purified by HPLC (yield=60%). $^1$H NMR (DMSO-$d_6$, ppm): 10.73 (s, 1H), 9.09 (bs, 1H), 8.57 (d, 2H), 8.44 (d, 2H), 8.36 (d, 1H), 8.21 (d, 1H), 7.61 (m, 3H), 7.50 (s, 2H), 7.27 (d, 1H), 7.17 (d, 2H), 7.03 (d, 2H), 4.38 (d, 2H).

EXAMPLE 4

1-(4-Ethoxy-phenyl)-3-[4-(N'-cyano-N"-pyridin4-yl-guanidinomethyl)-phenyl]-urea (SBR-11-3831) was synthesized as follows N-(4-Amino-benzyl)-N'-cyano-N"-quinolin-5-yl-guanidine (100 mg, 0.380 mmol) and 1-ethoxy-4-isocyanato-benzene (61 mg,, 0.39 mmol) were dissolved in mixture of N,N-dimethylformamide (2.0 mL).and tetrahydrofuran (1.0 mL). Triethylamine (0.060 mL, 0.390 mmol) was added. The reaction mixture was shaken at room temperature for 12 hours. The solvent was removed in vacuo to give the title compound (yield=85%). $^1$H NMR (DMSO-$d_6$, ppm): 8.34 (br, s, 2H); 7.41–7.21 (m, 10H); 6.82–6.76 (m, 2H); 4.43 (s, 2H); 3.93 (dq, 2H); 1.28 (dt, 3H).

EXAMPLE 5

N-(4-Benzylamino-benzyl)-N'-cyano-N"-pyridin-4-yl-guanidine (SBR-11-3536) was synthesized as follows N-(4-Amino-benzyl)-N'-cyano-N"-quinolin-5-yl-guanidine (146 mg, 0.55 mmol), benzaldehyde (51 μl, 0.50 mmol), and sodium triacetoxyborohydride (159 mg, 0.750 mmol) were suspended in tetrahydrofuran (5.0 mL) and glacial acetic acid (0.2 mL) was added. The milky reaction mixture was stirred at room temperature for 18 hours and then quenched by addition of a saturated aqueous solution of sodium bicarbonate (5 mL). This solution was extracted with ethyl acetate (40 mL) and the organic layer was washed with 5% aqueous sodium bicarbonate (20 mL×2) and dried over anhydrous sodium sulfate. The solvent was removed in vacuo to give the crude product which was purified by flash chromatography (SiO$_2$, 10% methanol in chloroform). The pure product was obtained in 67% yield. $^1$H NMR (DMSO-d$_6$, ppm): 9.20 (bs, 1H), 8.34 (d, 2H), 8.12 (t, 1H), 7.10–7.38 (m, 7H), 7.02 (d, 2H), 6.54 (d, 2H), 6.25 (t, 1H), 4.26 (m, 4H).

EXAMPLE 6

N-(5-(10,11-Dihydro-5H-dibenzo[a,d]cyclohepten-5-yloxy)-pentyl)-N'-cyano-N"-pyridin-4-yl-guanidine (SBR-11-3776) was synthesized as follows In a reaction flask under nitrogen with magnetic stirring 2-(5-hydroxy-pentyl)-isoindole-1,3-dione (2.3 g, 10 mmol) was dissolved in 50 mL of methylene chloride. For synthesis of 2-(5-hydroxy-pentyl)-isoindole-1,3-dione, see Payne and Boger, Synth. Commun. 15, 1277–1290 (1985). Suberyl chloride (2.3 g, 10 mmol) was added followed by triethylamine (5 mL, 36 mmol) and the mixture was stirred at room temperature for 18 hours. The solvent was removed in vacuo and the residue was suspended in 150 mL of diethyl ether. The solid was removed by vacuum filtration and washed with 80 mL of diethyl ether. The filtrate and washings were combined and 50 mL of methanol was added to initiate precipitation. After chilling in an ice bath for 30 minutes a white crystalline product was collected by vacuum filtration. The solid was dissolved in 50 mL of ethanol and hydrazine hydrate (10 mL, 500 mmol) was added. The mixture was heated at reflux for 6 hours and then allowed to cool to room temperature. The solvent was removed in vacuo and the residue was treated with 20 mL of a 10% aqueous sodium hydroxide solution. The alkaline solution was extracted with three 50 mL portions of diethyl ether and the combined organics were dried over sodium sulfate. The solvent was evaporated to give 5-(10,11-dihydro-5H-dibenzo[a,d] cyclohepten-5-yloxy)-pentylamine as a clear oil in quantitative yield.

1-Cyano-2-methyl-3-pyridin-4-yl-isothiourea (573 mg, 3.00 mmol) and 5-(10,11-dihydro-5H-dibenzo[a,d] cyclohepten-5-yloxy)-pentylamine (886 mg, 3.00 mmol) were dissolved in pyridine (20 mL). Triethylamine (2 mL, 14 mmol) was added followed by (4-dimethylamino) pyridine (5.0 mg, 0.04 mmol). The reaction mixture was stirred at 86□ C. for 12 hours. After cooling to room temperature, the reaction mixture was diluted with diethyl ether (50 mL). The resulting precipitate was collected by filtration and washed with diethyl ether. The crude product was recrystalized from methanol and diethyl ether to give the desired product as a white crystalline solid (yield 85%). $^1$H NMR (CDCl$_3$, ppm): 8.54 (dd, 2H), 7.41–7.12 (m, 10H), 5.29 (s, 1H), 3.56–3.41 (m, 4H), 3.32 (dd, 2H), 3.05–2.95 (m, 2H), 1.71–1.41 (m, 6H).

EXAMPLE 7

N-Cyano-N'-[2-(4-naphthalen-1-ylmethyl-piperazin-1-yl)-ethyl]-N"-pyridin-4-yl-guanidine (SBR-11-4326) was synthesized as follows S-methyl-N-cyano-N'-pyridylisothiourea (3.84 g, 20 mmol) and 1-(2-aminoethyl)piperazine (2.89 ml, 22 mmol) were suspended in pyridine (8 mL) in a reaction flask equipped with magnetic stirring under nitrogen. Triethylamine (2.8 mL, 20 mmol) was added followed by (4-dimethylamino)-pyridine (cat., 100 mg). The reaction mixture became clear. It was stirred at 50–60° C. for 12 hours and cooled to room temperature. Ether (100 mL) was then added and precipitate formed. The precipitate was collected to give crude N-cyano-N'-(2-piperazin-1-yl-ethyl)-N"-pyridin-4-yl-guanidine which was used without further purification. ESMS 274.2 (M+1).

N-cyano-N'-(2-piperazin-1-yl-ethyl)-N"-pyridin-4-yl-guanidine (207 mg, 0.757 mmol) and 1-nathphylaldehyde (118 mg, 0.757 mmol) were suspended in a tetrahydrofuran (5 ml). Sodium triacetoxyborohydride (241 mg, 1.14 mmol) was added followed by glacial acetic acid (cat. 5 drops). The reaction mixture was stirred at room temperature for 12 hours and then quenched with saturated sodium bicarbonate (5 mL). The final product was extracted with 100 mL ethyl acetate. The organic layer was washed with 5% sodium bicarbonate (2×20 mL), then dried over anhydrous sodium sulfate. The solvent was removed in vacuo to give the crude product which was further purified by flash column chromatography (SiO$_2$, 10% MeOH in EtOAc). The pure title product was obtained in 35% yield in two steps. $^1$H-NMR ((CD$_3$OD, ppm): 8.38 (d, 2H), 8.26 (d, 1H), 7.81–7.86 (m, 3H), 7.40–7.50(m, 5H), 3.95 (s, 2H), 3.48 (t, 2H), 2.58 (m, 10H). ESMS 414.4 (M+1), 436.3 (M+23).

EXAMPLE 8

N-[2-(4-Benzhydryl-piperazin-1-yl)-ethyl]-N'-cyano-N"-pyridin-4-yl-guanidine (SBR-11-4408) was synthesized as follows N-cyano-N'-(2-piperazin-1-yl-ethyl)-N"-pyridin-4-yl-guanidine (273 mg, 1 mmol) (prepared using the procedure described in Example 7) and bromodiphenylmethane (247 mg, 1 mmol) was dissolved in dimethylformamide (1.5 mL), followed by the addition of triethylamine (0.21 mL, 1.5 mmol). The reaction solution was stirred at room temperature under nitrogen for 10–15 hours and then diluted with 100 mL ethyl acetate. The organic layer was washed with water (3×30 mL) and dried over anhydrous sodium sulfate. The solvent was removed in vacuo to give crude title product. The final product was further purified by flash column chromatography (SiO$_2$, 10% MeOH in EtOAc). The pure product was obtained in 50% yield in two steps. $^1$H-NMR (CD$_3$OD, ppm): 8.36 (d, 2H), 7.18–7.43 (m, 12H), 4.29 (s, 1H), 3.46 (t, 2H), 2.45–2.61 (m, 10H). ESMS 440.4 (M+1), 462.4 (M+23).

EXAMPLE 9

N-[2-(4-Benzhydryloxy-piperidin-1-yl)-ethyl]-N'-cyano-N"-pyridin-4-yl-guanidine (SBR-114483) was synthesized as follows To a round bottom flask, benzhydrol (1.84 g, 10 mmol, 1.0 eq.), 4-hydroxypiperidine (1.01 g, 10 mmol, 1.0 eq.), and p-toluenesulfonic acid monohydrate (2.09 g, 1.1 eq.) were suspended in toluene (400 ml). The mixture was refluxed with a Dean-Stark condenser for 3–4 hours. After cooling to room temperature, the solution was washed with 5% NaOH solution (2×20 ml), then with water (2×20 ml). The solution was then dried over anhydrous Na$_2$SO$_4$. The solvent was then removed under vacuum. The crude product, 4-benzhydryloxy-piperidine was obtained (2.46 g, 92.0% yield). $^1$H-NMR (CDCl$_3$, ppm): 7.10–7.25 (m, 10H), 5.41 (s, 1H), 3.48 (m, 1H), 3.13 (m, 2H), 2.78 (m, 2), 1.86 (m, 2H), 1.66 (m, 2H). ESMS 268.1 (M+1), 290.1 (M+23).

The mixture of 4-benzhydryloxy-piperidine (1.85 g, 3.4 mmol, 1.0 eq.), N-(2-bromoethyl)phthalimide (0.855 g, 3.4 mmol, 1.0 eq.), $K_2CO_3$ (0.705 g, 5.1 mmol, 1.5 eq.), and NaI (0.713 g, 4.8 mmol, 1.4 eq.) in 2-butanone (20 ml) was refluxed for 2–3 hours. The mixture was then cooled to room temperature. The white solid was filtered off and was washed with small amount of $CHCl_3$. The filtrates were combined and concentrated. The resulted residue was dissolved in $CHCl_3$ (100 ml). The solution was washed with water (3×10 ml), then dried over anhydrous $Na_2SO_4$. After removed all solvent, the crude product, 2-[2-(4-benzhydryloxy-piperidin-1-yl)-ethyl]-isoindole-1,3-dione was yielded (1.5 g, 100% yield). $^1$H-NMR ($CDCl_3$, ppm): 7.84 (m, 2H), 7.70 (m, 2H), 7.20–7.40 (m, 10H), 5.50 (s, 1H), 3.80 (t, 2H), 3.39 (m, 1H), 2.82 (m, 2H), 2.59 (t, 2H), 2.18 (m, 2H), 1.83 (m, 2H) 1.67 (m, 2H). ESMS 441.2 (M+1), 463.2 (M+23).

2-[2-(4-benzhydryloxy-piperidin-1-yl)-ethyl]-isoindole-1,3-dione (0.548 g, 1.24 mmol) was dissolved in ethanol (2 ml), followed by the addition of hydrazine hydrate (large excess, 2–3 ml). The solution was refluxed for 2 hours. The white solid was precipitated. After cooling to the room temperature, the white solid was filtered off and washed with small amount of ethanol. The filtrates were combined and concentrated. The resulted residue was dissolved in toluene (100 ml). The solution was washed with water (3×20 ml) and dried over anhydrous $Na_2SO_4$. After evaporated the solvent, the crude product, 2-(4-benzhydryloxy-piperidin-1-yl)-ethylamine was obtained (0.326 g, 84.4% yield). $^1$H-NMR ($CD_3OD$, ppm): 7.15–7.40 (m, 10H), 5.58 (s, 1H), 3.46 (m, 1H), 2.77 (m, 2H), 2.72 (t, 2H), 2.40 (t, 2H), 2.18 (m, 2H), 1.89 (m, 2H), 1.70 (m, 2H). ESMS 311.2 (M+1), 333.2 (M+23).

The solution of 2-(4-benzhydryloxy-piperidin-1-yl)-ethylamine (310 mg, 1 mmol) and S-methyl-N-cyano-N'-pyridylisothiourea (192 mg, 1 mmol) in isopropanol (2 ml) was stirred at room temperature overnight. The white solid was precipitated. The solid was collected and washed with small amount isopropanol and then with ether. The title compound was obtained (180 mg, 38.4% yield). $^1$H-NMR ($CD_3OD$, ppm): 8.38 (d, 2H), 7.41 (d, 2H), 7.20–7.40 (m, 10H), 5.60 (s, 1H), 3.52 (m, 1H), 3.48 (t, 2H), 2.88 (m, 2H), 2.61 (t, 2H), 2.34 (m, 2H), 1.92 (m, 2H), 1.76 (m 2H). ESMS 455.3 (M+1), 477.3 (M+23).

EXAMPLE 10

N-[2-(4-Benzhydryloxymethyl-piperidin-1-yl)-ethyl]-N'-cyano-N''-pyridin-4-yl-guanidine (SBR-114540) was synthesized as follows To the suspension of $LiAlH_4$ in THF (250 ml) at 0° C., the solution of ethyl isonipecotate (5.0 g, 32 mmol) in THF (100 ml) was added in drops. After the addition, the solution was stirred at room temperature overnight. The reaction flask was cooled in ice bath. Saturated $Na_2SO_4$ was added until no more gas released. The reaction was then filtered through a bed of celite to obtain clear solution. The solvent was removed under vacuum. The waxy solid piperidin-4-yl-methanol was obtained (3.1 g, 83% yield). The crude product will be used without further purification. ESMS 115.9 (M+1).

To a round bottom flask, benzhydrol (1.84 g, 10 mmol, 1.0 eq.), piperidin-4-yl-methanol (1.15 g, 10 mmol, 1.0 eq.), and p-toluenesulfonic acid monohydrate (2.09 g, 1.1 eq.) were suspended in toluene (400 ml). The mixture was refluxed with a Dean-Stark condenser for 3–4 hours. After cooling to room temperature, the solution was washed with 5% NaOH solution (2×20 ml), then with water (2×20 ml). The solution was then dried over anhydrous $Na_2SO_4$. The solvent was then removed under vacuum. The crude product 4-(1,1-diphenyl-methoxymethyl)-piperidine was obtained (2.33 g, 82.8% yield). ESMS 268.1 (M+1), 290.1 (M+23).

The mixture of 4-(1,1-diphenyl-methoxymethyl)-piperidine (0.760 g, 2.7 mmol, 1.0 eq.), N-(2-bromoethyl)phthalimide (0.686 g, 2.7 mmol, 1.0 eq.), $K_2CO_3$ (0.560 g, 4.1 mmol, 1.5 eq.), and NaI (0.567 g, 3.8 mmol, 1.4 eq.) in 2-butanone (10 ml) was refluxed for 2–3 hours. The mixture was then cooled to room temperature. The white solid was filtered off and was washed with small amount of $CHCl_3$. The filtrates were combined and concentrated. The resulted residue was dissolved in $CHCl_3$ (80 ml). The solution was washed with water (3×10 ml), then dried over anhydrous $Na_2SO_4$. After removed all solvent, the crude product 2-{2-[4-(1,1-diphenyl-methoxymethyl)-piperidin-1-yl]-ethyl}-isoindole-1,3-dione was yielded (0.980 g, 79.8% yield).

2-{2-[4-(1,1-Diphenyl-methoxymethyl)-piperidin-1-yl]-ethyl}-isoindole-1,3-dione (0.95 g, 2.1 mmol) was dissolved in ethanol (5 ml), followed by the addition of hydrazine hydrate (large excess, 2–3 ml). The solution was stirred at room temperature overnight. The white solid was precipitated. The white solid was filtered off and washed with small amount of ethanol. The filtrates were combined and concentrated. The resulted residue was dissolved in toluene (100 ml). The solution was washed with water (3×20 ml) and dried over anhydrous $Na_2SO_4$. After evaporated the solvent, the crude product 2-[4-(1,1-diphenyl-methoxymethyl)-piperidin-1-yl]-ethylamine was obtained (0.335 g, 49.4% yield).

The solution of 2-[4-(1,1-diphenyl-methoxymethyl)-piperidin-1-yl]-ethylamine (320 mg, 0.99 mmol) and S-methyl-N-cyano-N'-pyridylisothiourea (190 mg, 0.99 mmol) in isopropanol (2 ml) was stirred at room temperature overnight. The white solid was precipitated. 50 ml Ether was added and the mixture was stirred for 0.5 hr. The solid was collected and washed with small amount isopropanol and then with ether. The title compound was obtained (398 mg, 89.8% yield). $^1$H-NMR ($CD_3OD$, ppm): 8.24 (d, 2H), 7.20–7.45 (m, 12H), 5.37 (s, 1H), 3.48 (t, 2H), 3.34 (d, 2H), 3.05 (d, 2H), 2.14 (m, 2H), 1.81 (d, 2H), 1.72 (m, 1H), 1.45 (m, 2H). ESMS 469.3 (M+1), 491.2 (M+23).

EXAMPLE 11

N-{2-[4-(Benzhydryl-amino)-piperidin-1-yl]-ethyl}-N'-cyano-N''-pyridin4-yl-guanidine (SBR-11-4583) was synthesized as follows The mixture of 4-oxo-piperidine-1-carboxylic acid benzyl ester (0.98 ml, 5 mmol, 1.0 eq), aminodiphenylmethane (1.30 mL, 7.5 mmol, 1.5 eq), and $NaBH_3(OAc)_3$ was suspended in THF (10 mL). AcOH (10 drops as cat.) was added. The mixture was stirred at room temperature overnight. $NaHCO_3$ (saturated, 5 mL) was then added. The organic product was extracted with EtOAc (100 mL). The EtOAc layer was washed with H20 (3×20 mL), dried over anhydrous $Na_2SO_4$. The solvent was removed and the crude product 4-Oxo-piperidine-1-carboxylic acid benzyl ester was obtained (2.79 g). The crude product was used without further purification.

The 4-oxo-piperidine-1-carboxylic acid benzyl ester (crude, 2.7 g) was dissolved in HOAc, followed by the addition of the solution of HBr in HOAc (30%). (1.4 mL, 1.05 eq). The solution was stirred at room temperature overnight. The solid was precipitated. About 50 mL ether was added and the mixture was stirred for a while. The solid was collected and washed with ether. The crude product benzhydryl-piperidin-4-yl-amine hydrogen bromide salt was yielded (2.7 g).

The mixture of benzhydryl-piperidin-4-yl-amine hydrogen bromide salt (1.74 g, 5 mmol, 1.0 eq.), N-(2-bromoethyl)phthalimide (1.27 g, 5 mmol, 1.0 eq.), $K_2CO_3$ (1.73 g, 12.5 mmol, 2.5 eq.), and NaI (1.05 g, 7.0 mmol, 1.4 eq.) in 2-butanone (20 ml) was refluxed for 2-3 hours. The mixture was then cooled to room temperature. The white solid was filtered off and was washed with small amount of $CHCl_3$. The filtrates were combined and concentrated. The resulted residue was dissolved in $CHCl_3$ (100 ml). The solution was washed with water (3×20 ml), then dried over anhydrous $Na_2SO_4$. After removed all solvent, the crude product 2-{2-[4-(benzhydryl-amino)-piperidin-1-yl]-ethyl}-isoindole-1,3-dione was yielded (2.70 g).

The crude 2-{2-[4-(benzhydryl-amino)-piperidin-1-yl]-ethyl}-isoindole-1,3-dione (2.70 g) was dissolved in ethanol (5 ml), followed by the addition of hydrazine hydrate (large excess, 2–3 ml). The solution was stirred at room temperature overnight. The white solid was precipitated. The white solid was filtered off and washed with small amount of ethanol. The filtrates were combined and concentrated. The resulted residue was dissolved in toluene (100 ml). The solution was washed with water (3×15 ml) and dried over anhydrous $Na_2SO_4$. After evaporated the solvent, the crude product [1-(2-amino-ethyl)-piperidin-4-yl]-benzhydryl-amine was obtained (0.150 g, 7.9% yield).

The solution of [1-(2-amino-ethyl)-piperidin-4-yl]-benzhydryl-amine (150 mg, 0.485 mmol) and S-methyl-N-cyano-N'-pyridylisothiourea (93 mg, 0.485 mmol) in isopropanol (2 ml) was stirred at room temperature overnight. All the solvent was removed. The final product was purified by column (10% methanol in EtOAc). The title compound was obtained (74 mg, 33.6% yield). $^1$H-NMR ($CD_3OD$, ppm): 8.38 (d, 2H), 7.15–7.50 (m, 12H), 5.05 (s, 1H), 3.46 (t, 2H), 2.98 (d, 2H), 2.57 (t, 2H), 2.48 (m, 1H), 2.04 (m, 4H), 1.54 (m, 2H), ESMS 454.2 (M+1), 476.3 (M+23).

EXAMPLE 12

N-[3-(4-Benzhydryl-piperazin-1-yl)-propyl]-N'-cyano-N"-pyridin-4-yl-guanidine (SBR-11-4629) was synthesized as follows The mixture of 1-(diphenylmethyl)piperazine (505 mg, 2 mmol, 1.0 eq.), N-(2-bromoethyl)phthalimide (508 mg, 2 mmol, 1.0 eq.), $K_2CO_3$ (415 g, 3 mmol, 1.5 eq.), and NaI (420 g, 2.8 mmol, 1.4 eq.) in 2-butanone (10 ml) was refluxed for 2–3 hours. The mixture was then cooled to room temperature. The white solid was filtered off and was washed with small amount of $CHCl_3$. The filtrates were combined and concentrated. The resulted residue was dissolved in $CHCl_3$ (100 ml). The solution was washed with water (3×10 ml), then dried over anhydrous $Na_2SO_4$. After removed all solvent, the crude product 2-[3-(4-benzhydryl-piperazin-1-yl)-propyl]-isoindole-1,3-dione was yielded (935 mg, 110% yield).

The crude 2-[3-(4-benzhydryl-piperazin-1-yl)-propyl]-isoindole-1,3-dione (930 mg) was dissolved in ethanol (2 ml), followed by the addition of hydrazine hydrate (large excess, 2–3 ml). The solution was stirred at room temperature overnight. The white solid was precipitated. The white solid was filtered off and washed with small amount of ethanol. The filtrates were combined and concentrated. The resulted residue was dissolved in toluene (100 ml). The solution was washed with water (3×15 ml) and dried over anhydrous $Na_2SO_4$. After evaporated the solvent, the crude product 3-(4-benzhydryl-piperazin-1-yl)-propylamine was obtained (276 mg, 42.7% yield).

The solution of 3-(4-benzhydryl-piperazin-1-yl)-propylamine (275 mg, 0.834 mmol) and S-methyl-N-cyano-N'-pyridylisothiourea (160 mg, 0.834 mmol) in isopropanol (2 ml) was stirred at room temperature overnight. The white solid was precipitated. 50 ml Ether was added and the mixture was stirred for 0.5 hr. The solid was collected and washed with small amount isopropanol and then with ether. The title compound was obtained (235 mg, 59.5% yield). $^1$H-NMR ($CD_3OD$, ppm): 8.38 (d, 2H), 7.10–7.45 (m, 12H), 4.19 (s, 1H) 3.42 (t, 2H), 2.46 (m. 10H), 1.79 (m, 2H) ESMS 454.2(M+1), 476.2 (M+23).

EXAMPLE 13

N-[2-(4-Benzhydrylsulfanyl-piperidin-1-yl)-ethyl]-N'-cyano-N"-pyridin-4-yl-guanidine (SBR-11-4630) was synthesized as follows $H_2S$ gas bubbled through 1-methyl-4-piperidine (30 g, 0.265 mol) in isopropanol (75 mL) maintained at ice bath. After an hour, the mixture was filtered to give 6.5 g of the gem-dithiol. The filtrate was treated with $H_2S$ gas for another 2 hrs to give another 8.9 g. The filtrate was continuously treated with $H_2S$ gas for 2–3 hrs at the ice bath. The $H_2S$ gas was removed and the mixture was stirred at room temperature overnight. Filtration gave a further 7.5 g of gem-dithiol. The total yield is 22.9 g. The gem-dithiol was dried in the dark overnight. The gem-dithiol (10 g, 55.2 mmol) was added in small portions to as stirred suspension of $NaBH_4$ (2.5 g, 65.9 mmol) in isopropanol (25 mL) maintained at ice bath. After the addition, the mixture was stirred for 0.5 hr at the ice bath, then at room temperature overnight. The mixture was refluxed for 2 hours, cooled, and concentrated. The resulted residue was diluted with water and ether. The ether layer was separated and the aqueous layer was extracted with ether. Both ether fractions were combined and washed with brine and dried over $Na_2SO_4$. The solvent was removed and the final product 1-methyl-4-mercaptopiperidine was obtained from distillation under pressure (5.2 g).

The mixture of 1-methyl-mercaptopiperidine (0.350 g, 2.67 mmol, 1.1 eq.), bromodiphenylmethane (0.599 g, 2.42 mmol, 1.0 eq.), and $K_2CO_3$ (0.502 g, 3.63 mmol, 1.5 eq.) was suspended in acetone and heated at 40–50° C. for 3 days. Then, the mixture was refluxed for 12 hrs. The mixture was cooled to room temperature and the solid was filtered off. The solid was washed with small amount of acetone. The filtrates were combined and the solvent was removed to afford the product 4-benzhydrylsulfanyl-1-methyl-piperidine (0.353 g, 49.0%).

The solution of 4-benzhydrylsulfanyl-1-methyl-piperidine (350 mg, 1.18 mmol) and ethyl chloroformate (0.33 mL, 3.54 mmol, 3 eq.) in toluene (15 ml) was refluxed for 5 hrs. The solution was cooled to room temperature and then washed with diluted HCl (2.0 N, 2×5 mL). The solution was dried over anhydrous $Na_2SO_4$. The solvent was moved and the crude product 4-benzhydrylsulfanyl-piperidine-1-carboxylic acid ethyl ester was yielded (322 mg, 76.8% yield).

The solution of 4bezhydrylsulfanyl-piperidine-1-carboxylic acid ethyl ester (320 mg, 0.9 mmol) and 40%

NaOH (prepared from 216 mg NaOH and 0.33 ml H$_2$0) in EtOH (10 mL) was refluxed overnight. After the removal of the solvent, the resulted residue was diluted with water and extracted with ether. The ether layer was washed with diluted HCl (0.2 N). The aqueous fractions were combined and made alkaline with K$_2$CO$_3$ and then extracted with EtOAc. The EtOAc layer was washed with water, dried over Na2SO4 and evaporated to afford 4-bnzhydrylsulfanyl-piperidine as oil (12 mg, 4.7%).

The mixture of 4-benzhydrylsulfanyl-piperidine (12 mg, 0.0423 mmol, 1.0 eq.), N-(2-bromoethyl)phthalimide (11 mg, 0.0423 mmol, 1.0 eq.), K$_2$CO$_3$ (9 mg, 0.0635 mmol, 1.5 eq.), and NaI (9 mg, 0.0600 mmol, 1.4 eq.) in 2-butanone (5 ml) was refluxed for 2–3 hours. The mixture was then cooled to room temperature. The solvent was removed and the resulted residue was dissolved in CHCl$_3$ (25 ml). The solution was washed with water (3×5 ml), then dried over anhydrous Na$_2$SO$_4$. After removed all solvent, the crude product 2-[2-(4-benzhydrylsulfanyl-piperidin-1-yl)-ethyl]-isoindole-1,3-dione was yielded (15 mg).

The crude 2-[2-(4-benzhydrylsulfanyl-piperidin-1-yl)-ethyl]-isoindole-1,3-dione (930 mg) was dissolved in ethanol (0.5 ml), followed by the addition of hydrazine hydrate (large excess, 1 ml). The solution was stirred at room temperature overnight. The white solid was precipitated. The mixture was diluted with 50 ml toluene and the toluene layer was washed with was washed with water (3×5 ml) and dried over anhydrous Na$_2$SO$_4$. After evaporated the solvent, the crude 2-(4-benzhydrylsulfanyl-piperidin-1-yl)-ethylamine was obtained (10 mg).

The solution of 2-(4-benzhydrylsulfanyl-piperidin-1-yl)-ethylamine (10 mg, 0.0306 mmol) and S-methyl-N-cyano-N'-pyridylisothiourea (6 mg, 0.0306 mmol) in isopropanol (1 mL) was stirred at room temperature overnight. All the solvent was removed and the final product was purified by pre-HPLC (AcCN/methanol with 0.05% TFA). The title compound was obtained (3 mg 20.8% yield). $^1$H-NMR (CD$_3$OD, ppm): 8.56 (d, 2H), 7.68 (d, 2H), 7.20–7.50 (m, 10H), 5.38 (s, 1H), 3.85 (t, 2H), 3.68 (m, 1H), 2.95 (m, 2H), 2.66 (m, 2H), 2.19 (m, 2H), 1.85 (m, 2H). ESMS 471.2 (M+1), 493.2 (M+23).

EXAMPLE 14

N-{2-[2-(2-Chloro-phenoxy)-ethoxy]-ethyl}-N'-cyano-"-pyridin-4-yl-guanidine ( SBR-11-4435) was synthesized as follows To a reaction flask, 2-(2-aminoethoxy)ethanol (5.78 g, 55 mmol) and S-methyl-N-cyano-N'-pyridylisothiourea (9.60 g, 50 mmol) were suspended in pyridine (40 mL). Triethylamine (7 mL, 50 mmol) was added followed by (4-dimethylamino)pyridine (cat., 100 mg). The reaction mixture became clear solution, which was stirred at 50–60° C. for 10 hours. The reaction mixture was then cooled to room temperature. Ether (200 mL) was added and the resulting solid was collected to give N-[2-(2-hydroxyethoxy)-ethyl]-N'-cyano-N"-pyridin-4-yl-guanidine (12.0 g, 48 mmol, 96%) as a white solid which was used without further purification.

N-[2-(2-hydroxyethoxy)-ethyl]-N'-cyano-N"-pyridin-4-yl-guanidine (0.50 g, 2.00 mmol) was dissolved in N-methylpiperidine (5 mL) with gentle heating. Tetrahydrofuran (5 mL) and triphenylphosphine (0.629 g, 2.40 mmol) were added and the mixture was cooled to 0° C. Diethyl azodicarboxylate (0.42 g, 2.40 mmol) was added dropwise. The mixture was stirred at room temperature overnight. The solvents was then removed in vacuo. The final product was further purified by flash column chromatography (10% MeOH in ethyl acetate). The title product was given as a light brown viscous oil (0.40 g, 56% yield). $^1$H NMR (CDCl$_3$, ppm): 8.19 (br s, 2H), 6.88–7.70 (m, 8H), 4.23 (t, 2H), 4.00 (t, 2H), 3.86 (t, 2H), 3.69 (t, 2H). MS: 359.11 (calc'd); 360.2 (M+1); 382.2 (M+23).

EXAMPLE 15

N-{2-12-(4-Chloro-phenoxy)-ethoxy]-ethyl}-N'-cyano-N"-pyridin-4-yl-guanidine (SBR-11-4433) was synthesized as follows 2-(2-Aminoethoxy)ethanol (5.26 g, 50 mmol) and sodium hydroxide (2.1 g, 52.5 mmol) were dissolved in water (200 mL). The resulted solution was cooled in ice bath, followed by the dropwise addition of benzyl chloroformate. After the addition, the reaction mixture was continuously stirred in ice bath for another hour. The desired product was extracted with ethyl acetate (EtOAc, 200 mL). The EtOAc layer was washed with water (3×100 mL) and then dried over anhydrous sodium sulfate. The solvent was removed in vacuo to yield the crude product. The product was further purified by flash column chromatography (SiO$_2$, 1:2 Hexane:EtOAc) to give [2-(2-hydroxy-ethoxy)-ethyl]-carbamic acid benzyl ester as a clear oil (8.07 g, 67.5% yield). $^1$H-NMR (CDCl$_3$, ppm) 7.35 (m, 5H), 5.34 (b, 1H), 5.10 (s, 2H), 3.71 (m, 2H), 3.56 (m, 4H), 3.41 (m, 2H), 2.20 (b 1H),. ESMS 240.0 (M+1).

[2-(2-Hydroxy-ethoxy)-ethyl]-carbamic acid benzyl ester (2.39 g, 10 mmol), 4-chlorophenol (1.29 g, 10 mmol), and triphenylphosphine (2.89 g, 11 mmol) were dissolved in tetrahydrofuran (50 ml), followed by the dropwise addition of diethylazodicarboxylate (1.73 ml, 11 mmol). After the addition, the reaction solution was stirred at room temperature for 10–12 hours. The solvent was then removed in vacuo. The remaining residue was stirred in 30% EtOAc in hexane (200 mL) for 10 minutes and a white solid was formed. This solid was then filtered and washed with 30% EtOAc in hexane (3×20 mL). The filtrates were combined and the solvents were removed in vacuo. The remaining residue was purified by flash column chromatography (SiO$_2$, 2:1 hexane:EtOAc) to give {2-[2-(4-chloro-phenoxy)-ethoxy]-ethyl}-carbamic acid benzyl ester as clear solid (3.49 g, 99.8% yield). $^1$H-NMR (CDCl$_3$, ppm) 7.35 (m, 5H), 7.20 (d, 2H), 6.82 (d, 2H), 5.22 (b, 1H), 5.10 (s, 2H), 4.07 (t, 2H), 3.80 (t, 2H), 3.62 (t, 2H), 3.41 (q, 2H). ESMS 350.1 (M+l), 372.1 (M+23).

{2-[2-(4-Chloro-phenoxy)-ethoxy]-ethyl}-carbamic acid benzyl ester (3.49 g, 10 mmol) was suspended in 10 mL glacial acetic acid. A solution of 30 wt % hydrogen bromide in glacial acetic acid was added and the reaction mixture was stirred at room temperature for 10 hours. Ether (100 mL) was added to precipitate 2-[2-(4-chloro-phenoxy)-ethoxy]-ethylamine hydrobromide salt as a white solid which was then collected and washed with ether (3×10 mL) (1.55 g, 52.3% yield). $^1$H-NMR (CD$_3$OD, ppm) 7.26 (d, 2H), 6.93 (d, 2H), 4.15 (t, 2H), 3.88 (t, 2H), 3.78 (t, 2H), 3.15 (t, 2H). ESMS 216.0 (M+1).

To a reaction flask, S-methyl-N-cyano-N'-pyridylisothiourea (0.577 g, 3 mmol) and 2-[2-(4-chloro-phenoxy)ethoxy]ethylamine hydrobromide salt (0.979 g, 3.3 mmol) were suspended in pyridine (3 mL). Triethylamine (0.84 1L, 6 mmol) was added followed by (4-dimethylamino)-pyridine (cat., 50 mg). The reaction mixture became clear solution, which was stirred at 50–60° C.

for 12 hours. The reaction mixture was then cooled to room temperature. Ether (50 mL) was added to precipitate the desired product, which was then purified by crystallization from MeOH/H$_2$O (0.86 g, 79.7% yield). $^1$H-NMR (CD$_3$OD, ppm): 8.33 (d, 2H), 7.33 (m, 6H), 7.20 (m, 6H), 3.64 (t, 2H), 3.58 (m, 4H), 3.41 (t, 2H), ESMS 444.3 (M+1), 466.3 (M+23).

EXAMPLE 16

N-{2-[2-(10,11-Dihydro-5H-dibenzo[a,d]-cyclohepten-5-yloxy)-ethoxy]-ethyl}-N'-cyano-N"-pyridin-4-yl-guanidine (SBR-11-4416) was synthesized as follows To a solution of 2-(2-aminoethoxy)ethanol (10.51 g, 100 mmol, 1.00 equiv) in 50 mL MeOH at 0° C. was slowly added ethyl trifluoroacetate (17.0 g, 120 mmol, 1.20 equiv). The mixture was stirred at room temperature for 5 hours. Solvents were then removed to yield 2-(2-N-trifluoroacetyl-aminoethoxy)ethanol as viscous colorless oil (20.0 g, 100%).

2-(2-N-trifluoroacetyl-aminoethoxy)ethanol (5.0 g, 25 mmol, 1.00 equiv) and 5-chlorodibenzosuberane (5.72 g, 25 mmol, 1.00 equiv) were dissolved in 50 1L CH$_2$Cl$_2$. Triethylamine (3.03 g, 30 mmol, 1.20 equiv) was added to the solution at room temperature. The mixture was stirred at room temperature for 3 hours. The solvent was removed in vacuo. The resulted residue was diluted with ethyl acetate (300 mL) The solvent was removed in vacuo to yield 5-[2-(2-N-trifluoroacetylaminoethoxy)ethoxy] dibenzosuberane as viscous colorless oil which was treated with 30 mL 2M NaOH in 60 mL MeOH at room temperature for 4 hours. Most of solvent was removed on rotary evaporator. EtOAc/aqueous workup yielded 5-[2-(2-aminoethoxy) ethoxy]-dibenzosuberane as a light yellow viscous oil. [M+H] calculated: 297.17, found: 298.2.

The crude product obtained above and S-methyl-N-cyano-N'-pyridylisothiourea (4.85 g, 25 mmol, 1.00 equiv) were dissolved in pyridine (40 mL), followed by the addition of triethylamine (3.5 mL, 25 mmol, 1.00 equiv) and (4-dimethylamino)pyridine (cat., 100 mg). The reaction mixture was stirred at 50–55° C. for 10 hours. Ether (100 mL) was added and precipitate was formed, which was then collected and washed with ether (3×50 mL). The final product was purified by flash column chromatography (10% methanol in ethyl acetate) to yield the title product (10.0 g, 22.7 mmol, 91%). $^1$H-NMR (CDCl$_3$, ppm): 8.22 (d, 2H), 7.09–7.28 (m, 12H), 5.29 (s, 1H), 3.74–3.77 (m, 2H), 3.62–3.68 (m, 4H), 3.46–3.55 (m, 4H), 2.87–2.95 (m, 2H). ESMS 442.4 (M+1), 462.4 (M+23).

EXAMPLE 17

N-{2-[2-(4-Methoxy-phenyl-sulfanyl)-ethoxyl-ethyl}-N'-cyano-N"-pyridin-4-yl-guanidine (SBR-11-4443) was synthesized as follows To a solution of 2-(2-aminoethoxy)ethanol (11.56 g, 110 mmol, 1.10 equiv) in 200 mL THF and 50 mL NaHCO$_3$ (saturated) at 0° C. was slowly added di-tert-butyl-dicarbonate (21.83 g, 100 mmol, 1.00 equiv). The mixture was stirred at room temperature for 5 hours. The solvent was removed in vacuo. The remaining residue was diluted with ethyl acetate (300 mL). The organic phase was washed with H$_2$O (3×100 mL) and dried over anhydrous sodium sulfate. The solvent was evaporated to yield 2-(2-N-Boc-aminoethoxy)ethanol as a viscous colorless oil (20.5 g, 100%).

2-(2-N-Boc-aminoethoxy)ethanol (12.38 g, 60.4 mmol, 1.00 equiv) and triethylamine (7.50 g, 72.5 mmol, 1.20 equiv) were dissolved in 100 mL CH$_2$Cl$_2$ at 0° C. Methanesulfonyl chloride (8.30 g, 72.50 mmol, 1.20 equiv) was slowly added to the solution. The mixture was stirred at room temperature for 3 hours. The reaction solution was washed with H$_2$O (3×30 mL) and dried over anhydrous sodium sulfate. The solvent was removed in vacuo to yield 2-(2-N-Boc-aminoethoxy)ethyl methanesulfonate as a viscous colorless oil.

2-(2-N-Boc-aminoethoxy)ethyl methanesulfonate (1.486 g, 5.25 mmol, 1.05 equiv) and 4-methoxybenzenethiol (0.71 g, 5.0 mmol, 1.0 equiv) were dissolved in 20 mL THF. 5 mL 2 M NaOH solution was added, followed by 1.0 g of Aliquat 336. The mixture was stirred at room temperature for 14 hours. The solution was concentrated to yield a light yellow viscous oil which was then treated with 2 mL TFA in 10 mL methylene chloride at room temperature for 2 hours. The solvent was removed on rotary evaporator. The residue was neutralized with excess 2 M NaOH solution. The product was extracted with ethyl acetate (150 mL). The ethyl acetate layer was washed with H$_2$O (3×30 mL) and dried over anhydrous sodium sulfate. The solution was concentrated in vacuo to yield 2-(2'-aminoethoxy)ethyl 4-methoxyphenyl sulfide as a light yellow viscous oil (crude). [M+H] calculated: 227.10, found: 228.0.

2-(2'-Aminoethoxy)ethyl 4methoxyphenyl sulfide obtained in the procedure described above and S-methyl-N-cyano-N'-pyridylisothiourea (0.768 g, 4.0 mmol, 0.80 equiv) were dissolved in pyridine (4 ml), followed by the addition of triethylamine (0.56 mL, 4.0 mmol, 1.00 equiv) and (4-dimethylamino)pyridine (cat., 50 mg). The reaction mixture was stirred at 50–55° C. for 10 hours. The reaction solution was then solidified by ether (50 mL). The solid was collected and washed with ether (3×10 mL). The final product was purified by flash column chromatography (10% MeOH in ethyl acetate) to yield the title product as viscous light yellow oil (1.43 g, 3.85 mmol, 96%). $^1$H-NMR (CDCl$_3$, ppm): 8.44 (d, 2H), 7.53 (d, 2H), 7.33 (d, 2H), 711 (br s, 2H), 6.84 (d, 2H), 3.80 (s, 3H), 3.62–3.75 (m, 6H), 3.06 (t, 2H). ESMS 372.1 (M+l), 394.2 (M+23).

EXAMPLE 18

N-[2-(10,11-Dihydro-5H-dibenzo[a,d]-cyclohepten-5-yloxy)-ethyl]-N-[2-(N'-cyano-N"-pyridin-4-yl-guanidino)-ethyl]-acetamide (SBR-11-4427) was synthesized as follows To a solution of 2-(2-aminoethylamino)ethanol (1.15 g, 11 mmol, 1.10 equiv) in 50 mL MeOH at 0° C. was slowly added ethyl trifluoroacetate (1.42 g, 10 mmol, 1.00 equiv). The mixture was stirred at room temperature for 5 hours. Solvents were then removed, and the residue was dissolved in 50 mL methylene chloride. Triethylamine (1.52 g, 15 mmol) was added followed by acetyl chloride (0.94 g, 12 mmol, 1.20 equiv). Removal of solvent yielded N-acetyl-N-(2-trifluoroacetylaminoethyl)-(2'-hydroxyethyl)amine (crude) as a white solid. This crude product was subjected to a series of reactions similar to those for SBR-11-4416. 0.60 g final product was isolated as a white solid after HPLC purification. $^1$H NMR (CDCl$_3$, ppm): 8.47(d, 2H), 7.99 (brs, 2H), 7.14–7.35 (m, 10H), 5.20 (s, 1H), 2.96–3.56 (m, 12H), 2.18 (s, 3H). MS: 482.24 (calc'd); 483.5 (M+1).

EXAMPLE 19

N-(3-{Methyl-13-(N'-cyano-N"-pyridin-4-yl-guanidino)propyl]-amino}-propyl)-2,2-diphenyl-acetamide (SBR-11-4491) was synthesized as follows To a solution of 3,3'-diamino-N-methyldipropylamine (3.05 g, 21.0 mmol, 7.0 equiv.) in 10 mL pyridine at room temperature was added slowly diphenylacetyl chloride (0.692 g, 3.0 mmol, 1.0 equiv.). The reaction mixture was stirred at room temperature overnight, diluted with 100 mL EtOAc, and washed with 3×40 mL water to wash away excess starting material. The organic layer was washed with 30 mL brine, dried over $K_2CO_3$, and concentrated to yield 3-amino-3'-diphenylacetylamino-N-methyldipropylamine as viscous yellow oil (crude 0.82 g, 80%, 2.40 mmol). [M+H] calculated: 340.24, found: 340.2.

The crude product obtained above and S-methyl-N-cyano-N'-pyridylisothiourea (0.46 g, 2.40 mmol) were dissolved in 5 ml pyridine. The mixture was stirred at 70° C. for 4 hours. Solvent was removed, and the residue was purified by preparative HPLC to yield the title compound as an off-white solid (0.24 g, 0.5 mmol, 21%). $^1$H-NMR (DMSO-d6, ppm): 9.58 (br s, 1H), 8.34 (d, 2H), 8.26 (M, 2H), 7.84 (br s, 2H), 7.20–7.30 (m, 10H), 4.90 (s, 1H), 3.26 (t, 2H), 3.08 (m, 2H), 2.25–2.30 (m, 4H), 2.08 (s, 3H), 1.51–1.63 (m, 4H). ESMS 484.3 (M+1), 506.3 (M+23).

EXAMPLE 20

Naphthalene-2-sulfonic acid (3-{methyl-[3-(N'-cyano-N"-pyridin-4-yl-guanidino)-propyl]-amino}-propyl)-amide (SBR-114492) was synthesized as follows To a solution of 3,3'-diamino-N-methyldipropylamine (3.05 g, 21.0 mmol, 7.0 equiv.) in 10 mL pyridine at room temperature was added slowly 2-naphthalenesulfonyl chloride (0.68 g, 3.0 mmol, 1.0 equiv.). The reaction mixture was stirred at room temperature overnight, diluted with 100 mL EtOAc, and washed with 3×40 mL water to wash away excess starting material. The organic layer was washed with 30 mL brine, dried over $K_2CO_3$, and concentrated to yield 3-amino-3'-(2-naphthalenesulfonyl)amino-N-methyldipropylamine as viscous colorless oil (crude 0.78 g, 77%, 2.32 mmol). [M+H] calculated: 336.18, found: 336.2.

The crude product obtained above and S-methyl-N-cyano-N'-pyridylisothiourea (0.45 g, 2.32 mmol) were dissolved in 5 ml pyridine. The mixture was stirred at 70° C. for 4 hours. Solvent was removed, and the residue was purified by preparative HPLC to yield the title compound as an off-white solid (0.21 g, 0.5 mmol, 19%). $^1$H-NMR (DMSO-$d_6$, ppm): 9.58 (br s, 1H), 8.42 (s, 1H), 8.32 (d, 2H), 8.14 (t, 2H), 8.03 (d, 1H), 7.77 (dd, 1H),, 7.63–7.72 (m, 3H), 7.16 (d, 2H), 3.21 (t, 2H), 2.79 (t, 2H), 2.23 (t, 4H), 2.02 (s, 3H), 1.58 (t, 2H), 1.48 (t, 2H). ESMS 480.3 (M+1), 502.3 (M+23).

EXAMPLE 21

N-[2-(2-Benzhydryloxy-ethylamino)-ethyl]-N'-cyano-N"-pyridin-4-yl-guanidine (SBR-11-4493) was synthesized as follows To a solution of 2-(2-aminoethylamino)ethanol (2.08 g, 20 mmol, 1.00 eq.) in 40 mL MeOH at 0° C. was slowly added ethyl trifluoroacetate (7.10 g, 50 mmol, 2.50 eq.). The mixture was stirred at room temperature for 3 hours. Solvent and excess ethyl trifluoroacetate were then removed to yield 2-[N-trifluoroacetyl-N-(2-N'-trifluoroacetyl-aminoethyl)-amino]-ethanol as viscous colorless oil (5.90 g, 100%).

2-[N-trifluoroacetyl-N-(2-N'-trifluoroacetyl-aminoethyl)-amino]-ethanol (2.95 g, 10 mmol, 1.00 eq.) and diphenyl-bromomethane (2.47 g, 10 mmol, 1.00 eq.) were dissolved in 50 mL $CH_2Cl_2$. Triethylamine (1.55 g, 15 mmol, 1.50 eq.) was added to the solution at room temperature. The mixture was stirred at room temperature overnight. Usual workup yielded colorless viscous oil which was treated with 20 mL 2M NaOH in 50 mL MeOH at room temperature for 3 hours. Most of solvents were removed on rotary evaporator. EtOAc/aqueous workup gave N-diphenylmethoxyethyl-ethylenediamine as colorless viscous oil (1.60 g, crude). [M+H] calculated: 271.17, found: 271.1.

The crude product N-diphenylmethoxyethyl-ethylenediamine obtained above (1.60 g, 6.0 mmol, 1.0 equiv.) and S-methyl-N-cyano-N'-pyridylisothiourea (0.576 g, 3.00 mmol, 0.5 equiv.) were dissolved in 5 ml pyridine. The mixture was stirred at 70° C. for 4 hours. Solvent was removed, and the residue was purified by preparative HPLC to yield the title compound as an off-white solid (0.80 g, 1.93 mmol, 64%). $^1$H-NMR (DMSO-$d_6$, ppm): 8.24 (d, 2H), 7.11–7.41 (m, 14H), 5.45 (s, 1H), 3.49 (t, 2H), 2.58–2.81 (m, 6H), 1.25 (br s, 1H). ESMS 415.2 (M+1), 437.3 (M+23).

EXAMPLE 22

N-{2–12-(4-Chloro-phenoxy)-ethylsulfanyl]-ethyl}-N'-cyano-N"-pyridin-4-yl-guanidine (SBR-11-4494) was synthesized as follows To a solution of 2-(2-aminoethylthio)ethanol (3.64 g, 30 mmol, 1.00 eq.) in 20 mL MeOH at 0° C. was slowly added ethyl trifluoroacetate (5.68 g, 40 mmol, 1.30 eq.). The mixture was stirred at room temperature for 4 hours. Solvent and excess ethyl trifluoroacetate were then removed to yield 2-(2-N-trifluoroacetyl-aminoethylthio)ethanol as red-brown viscous oil (6.50 g, 100%).

2-(2-N-trifluoroacetyl-aminoethylthio)ethanol (1.09 g, 5 mmol, 1.00 eq.), 4-chlorophenol (0.771 g, 6 mmol, 1.20 eq.), and $PPh_3$ (1.70 g, 6.50 mmol, 1.30 eq.) were dissolved in 15 mL THF, and the mixture was cooled down to 0° C. Diethyl azodicarboxylate (1.13 g, 6.50 mmol, 1.30 eq.) was added in drops. The mixture was stirred at room temperature for 24 hours, then treated with 5 mL 2 M NaOH and 10 mL MeOH for 2 hours. The mixture was concentrated to about 10 mL, diluted with 60 mL EtOAc, and washed with 2×10 mL 1M NaOH. The organic layer was diluted with 10 mL ether and 2 mL hexane, and washed with 3×20 mL 1M HCl. The combined acidic aqueous layer was treated with NaOH until pH>12, and extracted with 3×60 mL EtOAc. The combined EtOAc layer was dried over $K_2CO_3$, and concentrated to yield 2-[2-(4-chlorophenoxy)ethylthio)]ethylamine as light yellow viscous oil (crude, 0.98 g, 4.24 mmol, 85%). [M+H] calculated: 232.05, found: 232.0.

The crude product 2-[2-(4-chlorophenoxy)ethylthio)] ethylamine obtained above (0.98 g, 4.24 mmol, 1.06 equiv.) and S-methyl-N-cyano-N'-pyridylisothiourea (0.768 g, 4.00 mmol, 1.0 equiv.) were dissolved in 10 ml pyridine. The mixture was stirred at 70° C. for 4 hours. The mixture was diluted with 100 mL water. White solid was formed, collected and washed with 2×3 mL EtOAc. The title compound was obtained as a white solid (0.73 g, 1.95 mmol, 49%). $^1$H-NMR (DMSO-$d_6$, ppm): 9.50 (br s, 1H), 8.41 (d, 2H), 7.93 (br s, 1H), 7.32 (d, 2H), 7.27 (d, 2H), 6.98 (d, 2H), 4.14 (t, 3H), 3.49 (t, 2H), 2.92 (t, 2H), 2.80 (t, 2H). ESMS 376.1 (M+l), 398.1 (M+23).

EXAMPLE 23

N-[2-(2-Benzhydryloxy-ethylsulfanyl)ethyl]-N'-cyano-"-pyridin-4-yl-guanidine (SBR-11-4495) was synthesized as follows 2-(2-N-trifluoroacetyl-aminoethylthio)ethanol (1.09 g, 5.0 mmol, 1.00 eq.) and bromodiphenyl methane (1.236 g, 5.0 mmol, 1.00 eq.) were dissolved in 20 mL $CH_2Cl_2$. Triethylamine (0.556 g, 5.50 mmol, 1.10 eq.) was added to the solution at room temperature. The mixture was stirred at room temperature overnight. Solvent was removed and the residue was treated with 15 mL 2 M NaOH in 20 mL MeOH for 2 hours. The mixture was concentrated to about 20 ml, diluted with 100 ml EtOAc, and washed with 2×20 mL brine. The organic layer was diluted with 10 ml ether and 2 mL hexane, and washed with 3×20 mL 1M HCl. The combined acidic aqueous layer was treated with NaOH until pH>12, and extracted with 3×60 mL EtOAc. The combined EtOAc layer was dried over $K_2CO_3$, and concentrated to yield 2-(2-diphenylmethoxyethylthio)ethylamine as light brown viscous oil (crude, 1.10 g, 3.83 mmol, 77%). [M+H] calculated: 288.13, found: 288.1.

The crude product 2-(2-diphenylmethoxyethylthio) ethylamine obtained above (1.10 g, 3.83 mmol, 0.96 equiv.) and S-methyl-N-cyano-N'-pyridylisothiourea (0.768 g, 4.00 mmol, 1.0 equiv.) were dissolved in 10 ml pyridine. The mixture was stirred at 70° C. for 4 hours. The mixture was diluted with 100 mL water and extracted with 2×100 ml EtOAc. The organic layer was dried over $MgSO_4$, concentrated and vacuum dried. Recrystallization in $CH_2Cl_2$/EtOAc yielded the title compound as a white solid (0.51 g, 1.18 mmol, 30%). $^1$H-NMR (DMSO-$d_6$, ppm): 9.55 (br s, 1H), 8;38 (d, 2H), 7.87 (br s, 1H), 7.23–7.39 (m, 12H), 5.50 (s, 1H), 3.57(t, 3H), 3.45 (t, 2H), 2.80 (t, 3H), 2.74 (t, 2H). ESMS 432.2 (M+1), 454. 2 (M+23).

EXAMPLE 24

N-(2-{2-[Bis-(4-fluoro-phenyl)methoxy]-ethoxy}-ethyl)-N'-cyano-N"-pyridin-4-yl-guanidine (SBR-11-4565) was synthesized as follows To a solution of 2-(2-N-trifluoroacetyl-aminoethoxy) ethanol (2.41 g, 12.0 mmol, 1.20 eq.) and 4,4'-difluorobenzhydrol (2.20 g, 10.0 mmol, 1.00 eq.) in 30 mL benzene was added slowly 1 mL 98% sulfuric acid at room temperature. The mixture was stirred at room temperature for 12 hours. The reaction mixture was diluted with 10 mL water, neutralized with NaOH until pH>13, and extracted with 3×40 mL EtOAc. The combined organic layer was concentrated, and the residue was treated with 10 mL 2M NaOH in 10 mL MeOH at room temperature for 4 hours. Most of solvents were removed on rotary evaporator. EtOAc/aqueous workup gave 2-[2-bis-(4-fluorophenyl) methoxyethoxy]ethylamine as light yellow viscous oil (crude, 2.42 g). [M+H] calculated: 308.12, found: 308.0.

The crude product 2-[2-bis-(4-fluorophenyl) methoxyethoxy]ethylamine obtained above (2.42 g, 7.89 mmol, 1.00 equiv.) and S-methyl-N-cyano-N'-pyridylisothiourea (1.514 g, 7.89 mmol, 1.0 equiv.) were dissolved in 10 ml pyridine. The mixture was stirred at 70° C. for 4 hours. Solvent was removed, and the residue was dissolved in 4 mL $CH_2Cl_2$. The 4 mL ether was added to the solution resulting formation of yellow solid which was removed by filtration. The solution was concentrated and the title product was isolated as yellow solid (0.54 g, 1.20 mmol, 12% from 4,4'-difluorobenzhydrol) after flash chromatography. $^1$H-NMR (DMSO-$d_6$, ppm): 8.55 (br s, 1H), 8.24 (d, 2H), 7.73 (br s, 1H), 7.61 (d, 2H), 7.21–7.24 (m, 4H), 6.95–7.00 (m, 4H), 5.34 (s, 1H), 3.58–3.80 (m, 8H). ESMS 452.3 (M+1), 474.2 (M+23).

EXAMPLES 25–148

Each of the pyridyl cyanoguanidine compounds named in the following table was prepared in accordance with the methods described above. $^1$H Nuclear magnetic resonance and mass spectroscopy data of each compound are also listed below. The columns "Mass (Cald)," "M+1, " "M (other)" refer to the calculated mass, the measured mass, and the mass associated with other ions, e.g., Na$^+$, of the exemplified compounds, respectively.

| Example | Compound ID | Name | NMR | Mass (Cald) | M + 1 | Mass(other) |
|---|---|---|---|---|---|---|
| 25 | SBR-11-2728 | N-(4-(N'-Cyano-N"-pyridin-4-yl-guanidinomethyl)-phenyl)-2-thiophen-2-yl-acetamide | (DMSO-$d_6$, ppm): 10.21 (s, 1H), 9.48(bs, 1H), 8.39(d, 2H), 8.32(t, 1H), 7.57(d, 2H), 7.39(t, 1H), 7.27(d, 2H), 7.22(d, 2H), 6.97(m, 2H), 4.43 (d, 2H) | 390.13 | 391.1 | 413.1 (M + 23) |
| 26 | SBR-11-2730 | N-(4-(N'-Cyano-N"-pyridin-4-yl-guanidinomethyl)-phenyl)-isonicotinamide | (DMSO-$d_6$, ppm): 10.52 (s, 1H), 9.56(bs, 1H), 8.78(d, 2H), 8.39(m, 2H), 7.85(d, 2H), 7.75 (d, 2H), 7.23(d, 2H), 7.21(d, 2H), 4.47(d, 2H) | 371.15 | 372.2 | |
| 27 | SBR-11-2744 | Benzoic acid 2-(4-(N'-cyano-N"-pyridin-4-yl-guanidinomethyl)-phenylcarbamoyl)-benzyl ester | (DMSO-$d_6$, ppm): 10.50 (s, 1H), 9.52(bs, 1H), 8.39(bs, 3H), 7.91(d, 2H), 7.51–7.69(m, 7H), 7.39(m, 2H), 7.26(d, 2H), 7.22(d, 2H), 5.53(s, 2H), 4.44(d, 2H) | 504.19 | 505.4 | 527.1 (M + 23) |
| 28 | SBR-11-2745 | 3-(4-Chloro-phenyl)-N-(4-(N'-cyano-N"-pyridin-4-yl-guanidinomethyl)-phenyl)-acrylamide | (DMSO-$d_6$, ppm): 10.25 (s, 1H), 9.50(bs, 1H), 8.40(d, 2H), 8.33(bs, 1H), 7.60–7.67(m, 4H), 7.50–7.55(m, 3H), 7.30 (d, 2H), 7.22(d, 2H), 6.82(d, 1H), 4.45(d, 2H) | 430.13 | 431.2 | 453.1 (M + 23) |
| 29 | SBR-11-2747 | 2-Dimethylamino-N- | (DMSO-$d_6$, ppm): 9.77(s, | 441.23 | 442.4 | 464.2 |

-continued

| Example | Compound ID | Name | NMR | Mass (Cald) | M + 1 | Mass(other) |
|---|---|---|---|---|---|---|
| | | (4-(N'-cyano-N"-pyridin-4-yl-guanidinomethyl)-phenyl)-3-phenyl-propionamide | 1H), 9.48(bs, 1H), 8.30 (d, 2H), 8.30(bs, 1H), 7.53(d, 2H), 7.14–7.25 (m, 9H), 4.41(d, 2H), 3.42(m, 1H), 3.05(m, 1H), 2.87(m, 1H), 2.32 (s, 6H) | | | (M + 23) |
| 30 | SBR-11-2748 | 2-Furan-2-yl-N-(4-(N'-cyano-N"-pyridin-4-yl-guanidinomethyl)-phenyl)-2-oxo-acetamide | (DMSO-$d_6$, ppm): 10.83 (s, 1H), 9.53(bs, 1H), 8.40(bs, 3H), 8.22(d, 1H), 7.90(d, 1H), 7.77 (d, H), 7.34(d, 2H), 7.22 (d, 2H), 6.84(m, 1H), 4.46(d, 2H) | 388.13 | 389.2 | 411.1 (M + 23) |
| 31 | SBR-11-2749 | 2-(6-Methoxy-naphthalen-2-yl)-N-(4-(N'-cyano-N"-pyridin-4-yl-guanidinomethyl)-phenyl)-propionamide | (DMSO-$d_6$, ppm): 10.13 (s, 1H), 9.03(bs, 1H), 8.54(d, 2H), 7.78(m, 3H), 7.58(d, 2H), 7.49 (m, 3H), 7.25(m, 3H), 7.15(d, 1H), 4.46(d, 2H), 3.96(q, 1H), 3.88(s, 3H), 1.48(d, 3H) | 478.21 | 479.4 | 501.3 (M + 23) |
| 32 | SBR-11-2750 | 2-Benzyl-N-(4-(N'-cyano-N"-pyridin-4-yl-guanidinomethyl)-phenyl)-benzamide | (DMSO-$d_6$, ppm): 10.38 (s, 1H), 9.52(bs, 1H), 8.41(d, 2H), 8.32(bs, 1H), 7.67(d, 2H), 7.31 (m, 13H), 4.44(d, 2H), 4.14(s, 2H) | 460.20 | 461.3 | 483.2 (M + 23) |
| 33 | SBR-11-2751 | 1-Methyl-1H-pyrrole-2-carboxylic acid (4-(N'-cyano-N"-pyridin-4-yl-guanidinomethyl)-phenyl)-amide | (DMSO-$d_6$, ppm): 9.75(s, 1H), 9.58(bs, 1H), 8.39 (d, 2H), 8.35(bs, 1H), 7.70(d, 2H), 7.27(d, 2H), 7.21(d, 2H), 7.01 (m, 2H), 6.08(m, 1H), 4.45(d, 2H), 3.87(s, 3H) | 373.17 | 374.3 | 396.2 (M + 23) |
| 34 | SBR-11-2752 | Pyridine-2-carboxylic acid (4-(N'-cyano-N"-pyridin-4-yl-guanidinomethyl)-phenyl)-amide | (DMSO-$d_6$, ppm): 10.64 (s, 1H), 9.52(bs, 1H), 8.75(d, 1H), 8.40(d, 2H), 8.35(bs, 1H), 8.18 (d, 1H), 8.08(t, 1H), 7.89 (d, 2H), 7.68(t, 1H), 7.33 (d, 2H), 7.23(d, 2H), 4.47(d, 2H) | 371.15 | 372.2 | 394.2 (M + 23) |
| 35 | SBR-11-2754 | N-(4-(N'-Cyano-N"-pyridin-4-yl-guanidinomethyl)-phenyl)-4-trifluoromethoxy-benzenesulfonamide | (DMSO-$d_6$, ppm): 10.30 (bs, 1H), 9.49(bs, 1H), 8.38(d, 2H), 8.22(bs, 1H), 7.75(d, 2H), 7.62 (d, 2H), 7.20(d, 4H), 7.08(d, 2H), 4.39(d, 2H) | 490.10 | 491.1 | |
| 36 | SBR-11-2755 | 4-Chloro-N-(4-(N'-cyano-N"-pyridin-4-yl-guanidinomethyl)-phenyl)-benzenesulfonamide | (DMSO-$d_6$, ppm): 10.38 (bs, 1H), 9.45(bs, 1H), 8.38(bs, 2H), 8.25(bs, 1H), 7.74(d, 2H), 7.62 (d, 2H), 7.22(d, 4H), 7.08(d, 2H), 4.38(d, 2H) | 440.08 | 441.1 | 463.1 (M + 23) |
| 37 | SBR-11-2756 | N-(4-(4-(N'-Cyano-N"-pyridin-4-yl-guanidinomethyl)-phenylsulfamoyl)-phenyl)-acetamide | (DMSO-$d_6$, ppm): 10.29 (s, 1H), 10.19(s, 1H), 9.50(bs, 1H), 8.37(d, 2H), 8.26(t, 1H), 7.69(s, 4H), 7.18(m, 4H), 7.06 (d, 2H), 4.37(d, 2H), 2.06(s, 3H) | 463.14 | 464.2 | 486.2 (M + 23) |
| 38 | SBR-11-2757 | N-(4-(N'-Cyano-N"-pyridin-4-yl-guanidinomethyl)-phenyl)-benzenesulfonamide | (DMSO-$d_6$, ppm): 10.31 (s, 1H), 9.57(bs, 1H), 8.37(d, 2H), 8.25(t, 1H), 7.76(m, 2H), 7.55(m, 3H), 7.20(m, 4H), 7.05 (d, 2H), 4.36(d, 2H) | 406.12 | 407.1 | 429.1 (M + 23) |
| 39 | SBR-11-2758 | 4-Methyl-N-(4-(N'-cyano-N"-pyridin-4-yl-guanidinomethyl)-phenyl)-benzenesulfonamide | (DMSO-$d_6$, ppm): 10.22 (s, 1H), 9.52(bs, 1H), 8.37(d, 2H), 8.25(t, 1H), 7.63(d, 2H), 7.31(d, 2H), 7.17(m, 4H), 7.06 (d, 2H), 4.36(d, 2H), 2.32(s, 3H) | 420.14 | 421.2 | 443.2 (M + 23) |
| 40 | SBR-11-2759 | 4-Chloro-N-(4-(N'- | (DMSO-$d_6$, ppm): 10.69 | 485.07 | 486.1 | 508.1 |

-continued

| Example | Compound ID | Name | NMR | Mass (Cald) | M + 1 | Mass(other) |
|---|---|---|---|---|---|---|
| | | cyano-N"-pyridin-4-yl-guanidinomethyl)-phenyl)-3-nitro-benzenesulfonamide | (bs, 1H), 9.47(bs, 1H), 8.50(s, 1H), 8.40(d, 2H), 8.20(bs, 1H), 8.18(d, 1H), 7.89(s, 1H), 7.60(d, 2H), 7.21(d, 4H), 4.40 (d, 2H) | | | (M + 23) |
| 41 | SBR-11-2760 | Biphenyl-4-sulfonic acid (4-(N'-cyano-N"-pyridin-4-yl-guanidinomethyl)-phenyl)-amide | (DMSO-d$_6$, ppm): 10.38 (s, 1H), 9.48(bs, 1H), 8.36(d, 2H), 8.28(t, 1H), 7.83(s, 3H), 7.70(d, 2H), 7.46(m, 4H), 7.16(m, 6H), 4.36(d, 2H) | 482.15 | 483.2 | 505.2 (M + 23) |
| 42 | SBR-11-2761 | 2,5-Dichloro-N-(4-(N'-cyano-N"-pyridin-4-yl-guanidinomethyl)-phenyl)-benzenesulfonamide | (DMSO-d$_6$, ppm): 10.75 (bs, 1H), 9.60(bs, 1H), 8.38(d, 2H), 8.27(t, 1H), 7.98(s, 1H), 7.70(m, 2H), 7.30(m, 4H), 7.10 (d, 2H), 4.37(d, 2H) | 474.04 | 475.0 | 497.0 (M + 23) |
| 43 | SBR-11-2762 | Naphthalene-2-sulfonic acid (4-(N'-cyano-N"-pyridin-4-yl-guanidinomethyl)-phenyl)-amide | (DMSO-d$_6$, ppm): 10.41 (s, 1H), 9.53(bs, 1H), 8.44(s, 1H), 8.34(d, 2H), 8.21(t, 1H), 8.09(m, 2H), 7.98(d, 1H), 7.78 (d, 1H), 7.69(m, 2H), 7.15(m, 6H), 4.32(d, 2H) | 456.14 | 457.3 | 479.2 (M + 23) |
| 44 | SBR-11-2778 | 1-Methyl-cyclohexanecarboxylic acid (4-(N'-cyano-N"-pyridin-4-yl-guanidinomethyl)-phenyl)-amide | (DMSO-d$_6$, ppm): 9.49 (bs, 1H), 9.17(s, 1H), 8.38(d, 2H), 8.31(t, 1H), 7.60(d, 2H), 7.24(d, 2H), 7.20(bs, 2H), 4.43 (d, 2H), 2.06(m, 2H), 1.20–1.48(m, 8H), 1.17 (s, 3H) | 390.22 | 391.3 | |
| 45 | SBR-11-2780 | 6-Hydroxy-2,5,7,8-tetramethyl-chroman-2-carboxylic acid (4-(N'-cyano-N"-pyridin-4-yl-guanidinomethyl)-phenyl)-amide | (DMSO-d$_6$, ppm): 9.54 (bs, 1H), 9.38(s, 1H), 8.37(d, 2H), 8.28(bs, 1H), 7.57(d, 2H), 7.51(s, 1H), 7.26(d, 2H), 7.18 (bs, 2H), 4.34(d, 2H), 2.58(m, 2H), 2.32(m, 1H), 2.21(s, 3H), 2.10(s, 3H), 2.02(s, 3H), 1.82 (m, 1H), 1.52(s, 3H) | 498.24 | 499.2 | 521.1 (M + 23) |
| 46 | SBR-11-2781 | 1-Methyl-1H-indole-2-carboxylic acid (4-(N'-cyano-N"-pyridin-4-yl-guanidinomethyl)-phenyl)-amide | (DMSO-d$_6$, ppm): 10.33 (s, 1H), 9.50(bs, 1H), 8.40(bs, 2H), 8.33(bs, 1H), 7.74(d, 2H), 7.70 (d, 1H), 7.57(d, 1H), 7.32(d, 4H), 7.22(bs, 2H), 7.13(t, 1H), 4.48(d, 2H), 4.03(s, 3H) | 423.18 | 424.1 | |
| 47 | SBR-11-2782 | 5-Methyl-thiophene-2-carboxylic acid (4-(N'-cyano-N"-pyridin-4-yl-guanidinomethyl)-phenyl)-amide | (DMSO-d$_6$, ppm): 10.11 (s, 1H), 9.52(bs, 1H), 8.40(bs, 2H), 8.34(bs, 1H), 7.81(d, 1H), 7.68 (d, 2H), 7.30(d, 2H), 7.22(bs, 2H), 6.91(d, 2H), 4.45(d, 2H), 2.50(s, 3H) | 390.13 | 391.2 | |
| 48 | SBR-11-2783 | 8-Hydroxy-quinoline-2-carboxylic acid (4-(N'-cyano-N"-pyridin-4-yl-guanidinomethyl)-phenyl)-amide | (DMSO-d$_6$, ppm): 11.22 (s, 1H), 10.50(bs, 1H), 9.60(bs, 1H), 8.57(d, 1H), 8.40(bs, 2H), 8.27 (d, 1H), 7.59(t, 1H), 7.54 (d, 1H), 7.41(d, 2H), 7.23(m, 3H), 4.51(d, 2H), 3.50(bs, 1H) | 437.16 | 438.2 | |
| 49 | SBR-11-2887 | 2-Phenyl-ethenesulfonic acid (4-(N'-cyano-N"-pyridin-4-yl-guanidinomethyl)-phenyl)-amide | (DMSO-d$_6$, ppm): 10.08 (bs, 1H), 9.48(bs, 1H), 8.37(bs, 2H), 8.26(t, 1H), 7.68(m, 3H), 7.41 (m, 4H), 7.16–7.26(m, 6H), 4.38(d, 2H) | 432.14 | 433.3 | 455.2 (M + 23) |
| 50 | SBR-11-2888 | 4-Bromo-N-(4-(N'-cyano-N"-pyridin-4- | (DMSO-d$_6$, ppm): 10.37 (bs, 1H), 9.47(bs, 1H), | 484.05 | 485.0 | 507.0 (M + 23) |

-continued

| Example | Compound ID | Name | NMR | Mass (Cald) | M + 1 | Mass(other) |
|---|---|---|---|---|---|---|
| | | yl-guanidinomethyl)-phenyl)-benzenesulfonamide | 8.38(d, 2H), 8.24(d, 2H), 7.76(d, 2H), 7.66 (d, 2H), 7.20(d, 4H), 7.06(d, 2H), 4.37(d, 2H) | | | |
| 51 | SBR-11-2889 | 2,4,6-Trimethyl-N-(4-(N'-cyano-N''-pyridin-4-yl-guanidinomethyl)-phenyl)-benzenesulfonamide | (DMSO-$d_6$, ppm): 10.23 (s, 1H), 9.06(bs, 1H), 8.57(d, 2H), 7.49(bs, 2H), 7.19(d, 2H), 6.98 (m, 4H), 4.40(d, 2H), 2.52(s, 6H), 2.21(s, 3H) | 448.17 | 449.3 | 471.2 (M + 23) |
| 52 | SBR-11-2890 | 4-Fluoro-N-(4-(N'-cyano-N''-pyridin-4-yl-guanidinomethyl)-phenyl)-benzenesulfonamide | (DMSO-$d_6$, ppm): 10.33 (s, 1H), 9.50(bs, 1H), 8.37(bs, 2H), 8.24(bs, 1H), 7.81(m, 2H), 7.37 (m, 2H), 7.18(m, 4H), 7.06(d, 2H), 4.34(d, 2H) | 424.11 | 425.2 | 447.1 (M + 23) |
| 53 | SBR-11-2891 | 4-tert-Butyl-N-(4-(N'-cyano-N''-pyridin-4-yl-guanidinomethyl)-phenyl)-benzenesulfonamide | (DMSO-$d_6$, ppm): 10.31 (bs, 1H), 9.47(bs, 1H), 8.38(d, 2H), 8.25(t, 1H), 7.70(d, 2H), 7.55(d, 2H), 7.19(d, 4H), 7.09 (d, 2H), 4.36(d, 2H), 1.25(s, 9H) | 462.18 | 463.3 | 485.2 (M + 23) |
| 54 | SBR-11-2892 | Quinoline-8-sulfonic acid (4-(N'-cyano-N''-pyridin-4-yl-guanidinomethyl)-phenyl)-amide | (DMSO-$d_6$, ppm): 10.05 (bs, 1H), 9.45(bs, 1H), 9.12(d, 1H), 8.52(d, 1H), 8.33(m, 3H), 8.24 (d, 1H), 8.11(t, 1H), 7.71 (m, 2H), 7.11(bs, 2H), 7.03(s, 4H), 4.26(d, 2H) | 457.13 | 458.1 | 480.1 (M + 23) |
| 55 | SBR-11-2893 | 4-Iodo-N-(4-(N'-cyano-N''-pyridin-4-yl-guanidinomethyl)-phenyl)-benzenesulfonamide | (DMSO-$d_6$, ppm): 10.35 (bs, 1H), 9.47(bs, 1H), 8.38(d, 2H), 8.24(t, 1H), 7.91(d, 2H), 7.48(d, 2H), 7.19(d, 4H), 7.05 (d, 2H), 4.37(d, 2H) | 532.02 | 533.0 | |
| 56 | SBR-11-2894 | N-(4-(N'-Cyano-N''-pyridin-4-yl-guanidinomethyl)-phenyl)-C-phenyl-methanesulfonamide | (DMSO-$d_6$, ppm): 9.83 (bs, 1H), 9.52(bs, 1H), 8.39(d, 2H), 8.32(t, 1H), 7.16–7.34(m, 11H), 4.44 (bs, 4H) | 420.14 | 421.2 | 443.1 (M + 23) |
| 57 | SBR-11-2895 | 4-Methoxy-N-(4-(N'-cyano-N''-pyridin-4-yl-guanidinomethyl)-phenyl)-benzenesulfonamide | (DMSO-$d_6$, ppm): 10.13 (bs, 1H), 9.52(bs, 1H), 8.36(d, 2H), 8.23(t, 1H), 7.68(d, 2H), 7.17(d, 4H), 7.05(m, 4H), 4.36 (d, 2H), 3.78(s, 3H) | 436.13 | 437.2 | 459.1 (M + 23) |
| 58 | SBR-11-2896 | 2-Bromo-N-(4-(N'-cyano-N''-pyridin-4-yl-guanidinomethyl)-phenyl)-benzenesulfonamide | (DMSO-$d_6$, ppm): 10.62 (bs, 1H), 9.47(bs, 1H), 8.37(d, 2H), 8.21(t, 1H), 8.05(d, 1H), 7.79(d, 1H), 7.53(m, 2H), 7.16 (d, 4H), 7.06(d, 2H), 4.34(d, 2H) | 484.05 | 485.1 | 506.9 (M + 23) |
| 59 | SBR-11-2898 | N-(4-(N'-Cyano-N''-pyridin-4-yl-guanidinomethyl)-phenyl)-4-nitro-benzenesulfonamide | (DMSO-$d_6$, ppm): 10.62 (bs, 1H), 9.47(bs, 1H), 8.37(d, 4H), 8.24(t, 1H), 7.98(d, 2H), 7.20(d, 4H), 7.07(d, 2H), 4.37 (d, 2H) | 451.11 | 452.2 | 474.1 (M + 23) |
| 60 | SBR-11-2899 | N-(4-(N'-Cyano-N''-pyridin-4-yl-guanidinomethyl)-phenyl)-3-trifluoromethyl-benzenesulfonamide | (DMSO-$d_6$, ppm): 10.52 (s, 1H), 9.18(bs, 1H), 8.60(d, 2H), 8.02(m, 3H), 7.80(t, 1H), 7.53 (bs, 2H), 7.23(d, 2H), 7.12(d, 2H), 4.46(d, 2H) | 474.11 | 475.2 | 497.1 (M + 23) |
| 61 | SBR-11-2900 | Naphthalene-1-sulfonic acid (4-(N'-cyano-N''-pyridin-4-yl-guanidinomethyl)-phenyl)-amide | (DMSO-$d_6$, ppm): 10.74 (s, 1H), 9.10(bs, 1H), 8.72(d, 1H), 8.57(d, 2H), 8.23(m, 2H), 8.08 (d, 1H), 7.64(m, 4H), 7.50(bs, 2H), 7.12(d, 2H), 7.02(d, 2H), 4.38 (d, 2H) | 456.14 | 457.3 | 479.1 (M + 23) |
| 62 | SBR-11-3211 | 4-Chloro-N-(4-(N'-cyano-N''-(2-methyl- | (DMSO-$d_6$, ppm): 10.38 (bs, 1H), 9.45(bs, 1H), | 504.11 | 505 | 526.9 (M + 23) |

-continued

| Example | Compound ID | Name | NMR | Mass (Cald) | M + 1 | Mass(other) |
|---|---|---|---|---|---|---|
| | | quinolin-4-yl)-guanidinomethyl)-phenyl)-benzenesulfonamide | 8.25(bs, 1H), 8.08(m, 1H), 7.75(d, 1H), 7.70 (d, 2H), 7.62(d, 2H), 7.52(t, 1H), 7.29(t, 1H), 7.22(d, 2H), 7.08(d, 2H), 6.98(s, 1H), 4.40(d, 2H), 2.50(s, 3H) | | | |
| 63 | SBR-11-3401 | 4-Chloro-N-(4-(N'-cyano-N''-quinolin-5-yl-guanidinomethyl)-phenyl)-benzamide | (DMSO-d$_6$, ppm): 10.33 (s, 1H), 9.42(s, 1H), 8.95 (s, 1H), 8.18(m, 1H), 8.01(d, 2H), 7.46–7.86 (m, 9H), 7.27(d, 2H), 4.36(d, 2H) | 454.13 | 455.1 | |
| 64 | SBR-11-3402 | 4-Chloro-N-(4-(N'-cyano-N''-(2-methyl-quinolin-4-yl)-guanidinomethyl)-phenyl)-benzamide | (DMSO-d$_6$, ppm): 10.15 (bs, 1H), 9.44(bs, 1H), 8.22(bs, 1H), 8.08(m, 1H), 7.75(d, 1H), 7.69 (d, 2H), 7.55(d, 2H), 7.50(t, 1H), 7.28(t, 1H), 7.21(d, 2H), 7.10(d, 2H), 6.99(s, 1H), 4.41(d, 2H), 2.49(s, 3H) | 468.15 | 469 | |
| 65 | SBR-11-3538 | 1-Benzoyl-3-(4-(N'-cyano-N''-pyridin-4-yl-guanidinomethyl)-phenyl)-thiourea | (DMSO-d$_6$, ppm): 10.58(s, 1H), 9.45(s, 1H), 8.42(m, 3H), 7.91(d, 2H), 7.70(m, 3H), 7.58(d, 2H), 7.38(d, 2H), 7.20(s, 2H), 4.45(d, 2H) | 429.50 | 430.1 | |
| 66 | SBR-11-3547 | N-Cyano-N'-(4-((naphthalen-1-ylmethyl)-amino)-benzyl)-N''-pyridin-4-yl-guanidine | (DMSO-d$_6$, ppm): 9.42 (bs, 1H), 8.38(d, 2H), 8.14(d, 2H), 7.94(d, 1H), 7.82(d, 1H), 7.40–7.64(m, 4H), 7.18(d, 2H), 7.08(d, 2H), 6.62 (d, 2H), 6.28(t, 1H), 4.69 (d, 2H), 4.34(d, 2H) | 406.19 | 407.2 | |
| 67 | SBR-11-3548 | N-(4-(3,5-Di-tert-butyl-4-hydroxy-benzylamino)-benzyl)-N'-cyano-N''-pyridin-4-yl-guanidine | (DMSO-d$_6$, ppm): 9.41 (bs, 1H), 8.35(d, 2H), 8.13(bs, 1H), 7.18(m, 2H), 7.10(s, 2H), 7.06(d, 2H), 6.80(s, 1H), 6.60(d, 2H), 5.97(t, 1H), 4.32(d, 2H), 4.06(d, 2H), 1.38(s, 18H) | 484.3 | 485.3 | |
| 68 | SBR-11-3550 | 2-(6-Methoxy-naphthalen-2-yl)-N-(4-(N'-cyano-N''-pyridin-4-yl-guanidinomethyl)-phenyl)-propionamide | (DMSO-d$_6$, ppm): 10.16 (s, 1H); 9.04(bs, 1H); 8.54(d, 2H); 7.80(m, 3H); 7.60(d, 2H); 7.48(m, 3H); 7.23(d, 2H); 7.16(d, 2H); 4.44 (d, 2H); 3.99(q, 1H); 3.85(s, 3H); 1.50(d, 3H); | 478.21 | 479.4 | |
| 69 | SBR-11-3611 | Acetic acid 2-(4-(N'-cyano-N''-pyridin-4-yl-guanidinomethyl)-phenylcarbamoyl)-2,5,6,8-tetramethyl-chroman-7-yl ester | (CDCl$_3$, ppm) 8.36(bs. 1H); 7.98(d, 2H); 7.45(bs. 2H); 7.31(d, 2H); 7.21(d, 2H); 4.61(bs. 2H); 2.55(m, 2H); 2.26 (s, 3H); 2.16(s, 3H); 1.99 (s, 3H); 1.94(m, 2H); 1.89 (s, 3H); 1.50(s, 3H); | 540.61 | 541.3 | |
| 70 | SBR-11-3665 | N-(4-(2-Benzyloxy-benzylamino)-benzyl)-N'-cyano-N''-pyridin-4-yl-guanidine | (DMSO-d$_6$, ppm) 9.41 (bs, 1H), 8.32(d, 2H), 8.13(bs, 1H), 7.51–6.82 (several m, 16H), 6.53(d, 2H), 6.28(app t, 1H), 5.06(s, 2H), 4.32(d, 2H), 4.21(d, 2H) | 462.22 | 463.2 | |
| 71 | SBR-11-3666 | N-(4-(4-Chloro-benzylamino)-benzyl)-N'-cyano-N''-pyridin-4-yl-guanidine | (DMSO-d$_6$, ppm) 9.38 (bs, 1H), 8.37(d, 2H), 8.26(bs, 1H), 7.30(s, 4H), 7.20(bs, 2H), 7.03 (d, 2H), 6.51(d, 2H), 6.30(app t, 1H), 4.35(d, 2H), 4.21(d, 2H). | 390.14 | 391.1 | |
| 72 | SBR-11-3671 | Toluene-4-sulfonic acid 6-(N'-cyano-N''- | (CDCl$_3$/CD$_3$OD ppm): 8.38(d, 2H); 7.80(m, | 415.17 | 416.3 | |

| Example | Compound ID | Name | NMR | Mass (Cald) | M + 1 | Mass(other) |
|---|---|---|---|---|---|---|
| | | pyridin-4-yl-guanidino)-hexyl ester | 2H); 7.73(d, 2H); 3.96(t, 2H); 3.49(t, 2H); 2.43(s, 3H); 1.62(m, 4H); 1.33 (m, 4H); | | | |
| 73 | SBR-11-3703 | N-Cyano-N'-(4-((1-methyl-1H-indol-3-ylmethyl)-amino)-benzyl)-N''-pyridin-4-yl-guanidine | (DMSO-d$_6$, ppm): 9.40 (bs, 1H), 8.35(d, 2H), 8.14(bs, 1H), 7.75(d, 1H), 7.30–7.47(m, 3H), 7.28(s, 1H), 7.18(d, 2H), 7.06(d, 2H), 6.60(d, 2H), 5.95(t, 1H), 4.45(d, 2H), 4.07(d, 2H), 3.75(s, 3H) | 409.49 | | 432.1 (M + 23) |
| 74 | SBR-11-3722 | 5-Dimethylamino-naphthalene-1-sulfonic acid 6-(N'-cyano-N''-pyridin-4-yl-guanidino)-hexyl ester | (CDCl$_3$ ppm): 8.52(d, 1H); 8.37(d, 2H); 8.15 (m, 2H); 7.48(m, 2H); 7.19–7.11(m, 3H); 5.89 (br.t. 1H); 3.89(t, 2H); 3.22 9m, 2H); 2.81(s, 6H); 1.69–1.10(m, 8H); | 494.61 | 495.2 | |
| 75 | SBR-11-3723 | 6-(N'-Cyano-N''-pyridin-4-yl-guanidino)-hexanoic acid (3,7-dimethyl-oct-6-enyl)-amide | (DMSO-d$_6$, ppm): 8.38(bs, 2H), 7.85(bs, 1H), 7.70(bs, 1H), 7.20(s, 2H), 5.07(s, 1H), 3.25(s, 2H), 3.03(bs, 2H), 1.95(d, 4H), 1.64(s, 3H), 1.56(s, 3H) 1.51–1.13(m, 10H) | 412.57 | 413.3 | |
| 76 | SBR-11-3726 | 1-(4-(N'-Cyano-N''-pyridin-4-yl-guanidinomethyl)-phenyl)-3-(4-nitro-phenyl)-thiourea | (DMSO-d$_6$, ppm); 10.25(bs, 2H), 9.35(bs, 1H), 8.20(d, 2H), 8.18(bs, 1H), 8.00(d, 2H), 7.65(d, 2H), 7.28(d, 2H), 7.12(d, 2H), 7.05(bs, 2H), 4.22(d, 2H), | 446.49 | 447.1 | |
| 77 | SBR-11-3828 | N-Cyano-N'-pyridin-4-yl-N''-(2-(1-(2,4,6-trimethyl-benzenesulfonyl)-1H-imidazol-4-yl)-ethyl)-guanidine | (DMSO-d$_6$, ppm): 9.45(bs, 1), 8.40(m, 3H), 7.85(s, 1H), 7.40(s, 1H), 7.20(m, 3H), 7-15(s, 1H), 3.55(m, 2H), 2.74(t, 2H), 2.55(s, 6H), 2.30(s, 3H) | 437.52 | 438.1 | |
| 78 | SBR-11-3829 | N-(2-(1-(5-Dimethylamino-naphthalene-1-sulfonyl)-1H-imidazol-4-yl)-ethyl)-N'-cyano-N''-pyridin-4-yl-guanidine | (DMSO-d$_6$, ppm): 9.38(bs, 1H), 8.62(d, 1H), 8.52(s, 1H), 8.41(d, 1H), 8.29(m, 2H), 8.24(d, 1H), 7.83(bs, 1H), 7.75(m, 1H), 7.66(m, 1H), 7.56(s, 1H), 7.29(d, 1H), 7.08(bs, 1H), 3.47(m, 2H), 2.81(s, 6H), 2.69(t, 2H), | 488.57 | 489.2 | |
| 79 | SBR-11-3830 | N-Cyano-N'-(2-(1-(naphthalene-1-sulfonyl)-1H-imidazol-4-yl)-ethyl)-N''-pyridin-4-yl-guanidine | (DMSO-d$_6$, ppm): 9.40(bs, 1H), 8.65(d, 1H), 8.56(s, 1H), 8.44(m, 2H), 8.31(bs, 2H), 8.16(d, 2H), 7.80(m, 2H), 7.72(d, 1H), 7.59(s, 1H), 7.09(bs, 2H), 3.47(m, 2H), 2.70(bs, 2H) | 445.5 | 446.1 | |
| 80 | SBR-11-3863 | 1-(4-(N'-Cyano-N''-pyridin-4-yl-guanidinomethyl)-phenyl)-3-(3,4,5-trimethoxy-phenyl)-urea | (CD$_3$OD, ppm): 8.33(d, 2H); 7.42(d, 2H); 7.27 (m, 4H); 6.77(s, 2H); 4.51(s, 2H); 3.80(s, 6H); 3.71(s, 3H) | 475.5 | 476.3 | |
| 81 | SBR-11-3891 | N-(2-(3,4-Bis-benzyloxy-phenyl)-ethyl)-N'-cyano-N''-pyridin-4-yl-guanidine | (CDCl$_3$, ppm): 8.36 (dd, 2H), 7.45–7.24 (m, 13H), 6.80(dd, 2H), 5.14(d, 4H), 3.35 (dd, 2H), 2.79(app t 2H) | | 478.2 | 500.4 |
| 82 | SBR-11-3938 | 2,4,6-Trimethyl-N-(4-(N'-cyano-N''-pyridin-3-yl-guanidinomethyl)-phenyl)-benzenesulfonamide | (DMSO-d$_6$, ppm): 10.16 (bs, 1H), 9.18(bs, 1H), 8.41(s, 1H), 8.36(d, 1H), 7.79(t, 1H), 7.64(d, 1H), 7.37(m, 1H), 7.12(d, 2H), 6.97(m, 4H), 4.30 (d, 2H), 2.58(s, 6H), 2.24 (s, 3H) | 448.17 | 449.2 | 471.2 (M + 23) |
| 83 | SBR-11-3941 | N-(4-(N'-Cyano-N''- | (DMSO-d$_6$, ppm): 10.42 | 474.11 | 475.1 | 497.1 |

-continued

| Example | Compound ID | Name | NMR | Mass (Cald) | M + 1 | Mass(other) |
|---|---|---|---|---|---|---|
| | | pyridin-3-yl-guanidinomethyl)-phenyl)-3-trifluoromethyl-benzenesulfonamide | (s, 1H), 9.19(s, 1H), 8.44 (s, 1H), 8.36(d, 1H), 8.03 (m, 3H), 7.81(m, 2H), 7.64(d, 1H), 7.38(m, 1H), 7.21(d, 2H), 7.08 (d, 2H), 4.34(d, 2H) | | | (M + 23) |
| 84 | SBR-11-3955 | N-(2-(4-(10,11-Dihydro-5H-dibenzo(a, d)cyclo-hepten-5-yloxy)-phenyl)-ethyl)-N'-cyano-N"-pyridin-4-yl-guanidine | (CDCl$_3$, ppm): 8.02 (d, 2H), 7.95(d, 2H), 7.64–7.39(m, 8H), 7.38 (d, 2H), 6.84(d, 2H), 6.37(s, 1H), 3.96 (dd, 2H), 3.08–2.97 (m, 6H) | | 474.2 | |
| 85 | SBR-11-3956 | N-(2-(5-Benzyloxy-1H-indol-3-yl)-ethyl)-N'-methyl-N"-pyridin-4-yl-guanidine | (DMSO-d$_6$, ppm): 10.70(s, 1H), 8.86 (s, 1H), 8.46(d, 2H), 7.49–7.30(m, 8H), 7.17(d, 2H), 6.76 (d, 1H), 5.08(s, 2H), 3.24(dd, 2H), 2.96 (app t, 2H) | | 411.1 | |
| 86 | SBR-11-3982 | Naphthalene-1-sulfonic acid (4-(N'-cyano-N"-pyridin-4-yl-guanidino)-phenyl)-amide | (DMSO-d$_6$, ppm): 10.75(bs, 1H), 9.73(bs, 1H), 8.73(dd, 1H), 8.35(m, 1H), 8.21(d, 2H), 8.08(m, 1H), 7.65(m, 4H), 7.19(m, 1H), 7.14(d, 1H), 7.12(d, 1H), 7.01(d, 1H), 6.98(m, 1H), | 442.49 | 443 | |
| 87 | SBR-11-3983 | 5-Dimethylamino-naphthalene-1-sulfonic acid (4-(2-(N'-cyano-N"-pyridin-4-yl-guanidino)-ethyl)-phenyl)-amide | (DMSO-d$_6$, ppm): 10.60(bs, 1H), 9.35(bs, 1H), 8.42(d, 1H), 8.37(d, 1H), 8.28(d, 2H), 8.19(d, 1H), 7.77(t, 1H), 7.59(q, 2H), 7.23(d, 1H), 7.07(s, 1H), 7.04(s, 2H), 7.00(s, 2H), 6.97(s, 1H), 3.41(m, 2H), 2.74(bs, 6H), 2.69(t, 2H), | 513.62 | 514.2 | |
| 88 | SBR-11-3984 | 5-Dimethylamino-naphthalene-1-sulfonic acid (4-(N'-cyano-N"-pyridin-4-yl-guanidino)-2,5-dimethyl-phenyl)-amide | (DMSO-d$_6$, ppm): 9.85(s, 1H), 9.46(s, 1H), 8.46(d, 1H), 8.39(d, 2H), 8.01(d, 1H), 7.58(m, 2H), 7.27(m, 2H), 7.25(s, 1H), 6.90(s, 1H), 6.83(s, 1H), 2.83(s, 6H), 2.01(s, 3H), 1.81(s, 3H), | 513.62 | 514.2 | |
| 89 | SBR-11-3987 | 5-Dimethylamino-naphthalene-1-sulfonic acid (4-(N'-cyano-N"-pyridin-4-yl-guanidino)-phenyl)-amide | (DMSO-d$_6$, ppm): 10.65(bs, 1H), 9.74(bs, 1H), 8.45(d, 1H), 8.38(d, 1H), 8.33(bs, 1H), 8.22(d, 1H), 7.62(q, 2H), 7.25(d, 2H), 7.15(d, 4H), 7.02(d, 2H), 2.81(bs, 6H) | 485.56 | 486.2 | |
| 90 | SBR-11-3988 | 5-Dimethylamino-naphthalene-1-sulfonic acid (4-(N'-cyano-N"-(6-methoxy-pyridin-3-yl)-guanidinomethyl)-phenyl)-amide | (DMSO-d$_6$, ppm): 10.58(s, 1H), 8.87(s, 1H), 8.39(d, 1H), 8.32(d, 1H), 8.15(d, 1H), 7.93(d, 1H), 7.57(q, 2H), 7.47(dd, 1H), 7.35(bs, 1H), 7.20(d, 1H), 6.96(q, 4H), 6.75(d, 1H), 4.13(d, 2H), 3.79(s, 3H), 2.76(s, 6H) | 529.61 | 530.4 | |
| 91 | SBR-11-3996 | 5-Dimethylamino-naphthalene-1-sulfonic acid (4-(N'-(2-chloro-pyridin-3-yl)-N"-cyano-guanidinomethyl)-phenyl)-amide | (DMSO-d$_6$, ppm); 10.63(bs, 1H), 9.08(bs, 1H), 8.43(d, 1H), 8.36(d, 1H), 8.26(dd, 1H), 8.19(d, 1H), 7.77(d, 1H), 7.60(q, 2H), 7.42(dd, 1H), 7.24(d, 1H), 7.07(d, 2H), 7.02(d, 2H), 4.20(d, 2H), 2.79(s, 6H) | 534.03 | 534.2 | |
| 92 | SBR-11-3997 | 5-Dimethylamino-naphthalene-1-sulfonic acid (4-(N'-(4-amino-pyridin-3- | (DMSO-d$_6$, ppm): 8.43(d, 1H), 8.36(d, 1H), 8.19(d, 1H), 7.98(bs, 1H), 7.68(d, 1H), 7.60(q, 2H), | 514.6 | 515.2 | |

| Example | Compound ID | Name | NMR | Mass (Cald) | M + 1 | Mass(other) |
|---|---|---|---|---|---|---|
| | | yl)-N''-cyano-guanidinomethyl)-phenyl)-amide | 7.41(bs, 1H), 7.24(d, 1H), 7.07(d, 2H), 6.98(d, 2H), 6.85(bs, 1H), 5.16(bs, 2H), 4.18(d, 2H), 2.80(s, 6H) | | | |
| 93 | SBR-11-4077 | Octane-1-sulfonic acid (4-(N'-cyano-N''-pyridin-4-yl-guanidinomethyl)-phenyl)-amide | (DMSO-$d_6$, ppm): 9.80(s, 1H), 9.19(bs, 1H), 8.59 (d, 2H), 7.54(bs, 2H), 7.32(d, 2H), 7.19(d, 2H), 4.50, (d, 2H), 3.05 (app t, 2H), 1.64(pent, 2H), 1.30–1.20(m, 10H), 0.84(t, 3H) | 442.22 | 443.2 | |
| 94 | SBR-11-4078 | Hexadecane-1-sulfonic acid (4-(N'-cyano-N''-pyridin-4-yl-guanidinomethyl)-phenyl)-amide | (DMSO-$d_6$, ppm): 9.79(s, 1H), 9.07(br S, 1H), 8.57 (d, 2H), 7.51(br S, 2H), 7.30(d, 2H), 7.19(d, 2H), 4.48, (d, 2H), 3.04 (app t, 2H), 1.63(pent, 2H), 1.20(m, 26H), 0.87 (t, 3H) | 554.34 | 555.4 | |
| 95 | SBR-21-0660 | Piperidine-2-carboxylic acid (4-(N'-cyano-N''-pyridin-4-yl-guanidinomethyl)-phenyl)-amide | (DMSO-$d_6$, ppm): 10.15 (s, 1H), 9.53(bs, 1H), 9.20(bs, 1H), 8.40(d, 2H), 8.23(bs, 1H), 7.56 (d, 2H), 7.22(d, 4H), 4.38(d, 2H), 3.89(bs, 1H), 3.20(d, 1H), 2.88 (bs, 1H), 2.15(d, 1H), 1.63(m, 5H) | 377.20 | 378.2 | |
| 96 | SBR-21-2201 | Naphthalene-2-sulfonic acid 6-(N'-cyano-N''-pyridin-4-yl-guanidino)-hexyl ester | ($CDCl_3$ ppm): 8.80(d, 1H); 8.22(m, 3H); 8.07 (d, 1H); 7.89(m, 3H); 7.55(m, 4H); 3.53(m, 2H); 3.43(t, 2H); 1.61–1.43(m, 4H); 1.26(m, 4H); | 381.27 | 382 | |
| 97 | SBR-21-2419 | N-(4-((8-Hydroxy-quinolin-2-ylmethyl)-amino)-benzyl)-N'-cyano-N''-pyridin-4-yl-guanidine | (DMSO-$d_6$, ppm) 9.68 (bs, 1H), 9.37(bs, 1H), 8.39(d, 2H), 8.20(d, 2H), 8.17(m, 2H), 7.55 (d, 1H), 7.39(m, 2H), 7.21(d, 2H), 7.16(d, 2H), 6.68(d, 2H), 4.57 (d, 2H), 4.31(d, 2H) | 423.18 | | 446.1 (M + 23) |
| 98 | SBR-21-2803 | 1-(2-Methyl-4-nitro-phenyl)-3-(4-(N'-cyano-N''-pyridin-4-yl-guanidinomethyl)-phenyl)-urea | (DMSO-$d_6$): 9.44(bs. 1H); 8.38(d, 2H); 8.30(m, 2H); 8.10(d, 2H); 7.95(s, 1H); 7.47(d, 2H); 7.29(d, 2H); 7.19(m, 1H); 4.40(bs, 2H); 2.18(s, 3H): | 444.17 | 445.2 | |
| 99 | SBR-21-2804 | 1-(4-(N'-Cyano-N''-pyridin-4-yl-guanidinomethyl)-phenyl)-3-pentyl-urea | ($CD_3OD$, ppm): 8.30(d, 2H); 7.22(m, 4H); 7.06 (d, 2H), 4.38(s, 2H); 3.13 (t, 2H); 1.47–1.24(m, 6H); 0.88(t, 3H); | 379.46 | 380.2 | |
| 100 | SBR-21-2806 | 1-(4-(N'-Cyano-N''-pyridin-4-yl-guanidinomethyl)-phenyl)-3-(1-phenyl-ethyl)-urea | ($CD_3OD$, ppm): 8.34(d, 2H), 7.28–7.55(m, 7H), 7.25(m, 4H), 4.52(s, 2H), 3.50(q, 1H), 1.50 (d, 3H) | 413.2 | 414.3 | |
| 101 | SBR-21-2807 | 2-Methyl-N-(4-(N'-cyano-N''-pyridin-4-yl-guanidinomethyl)-phenyl)-4-trifluoromethyl-benzenesulfonamide | (DMSO-$d_6$, ppm): 9.03(bs 1H); 8.63(d, 1H); 8.54(d, 2H); 8.22(d, 2H); 7.50 (m, 2H); 7.29(d, 2H); 7.13(d, 2H); 4.48(d, 2H) | 519.46 | 520.2 | |
| 102 | SBR-11-2599 | N-(1-Benzyl-piperidin-4-yl)-N'-cyano-N''-pyridin-4-yl-guanidine | (DMSO-$d_6$, ppm): 9.44(bs, 1H); 8.37(d, 2H); 7.81(bs, 1H); 7.02–7.32(m, 7H); 3.68(m, 1H); 3.45(s, 2H); 2.79 (m, 2H); 2.01(m, 2H); 1.82(m, 2H); 1.52(m, 2H) | 334.19 | 335.3 | 357.3 (M + 23) |
| 103 | SBR-11-2733 | N-(4-(4-Benzhydryl- | (DMSO-$d_6$, ppm): 9.71 | 467.28 | 468.3 | 490.3 |

-continued

| Example | Compound ID | Name | NMR | Mass (Cald) | M + 1 | Mass(other) |
|---|---|---|---|---|---|---|
| | | piperazin-1-yl)-butyl)-N'-cyano-N"-pyridin-4-yl-guanidine | (bs, 1H); 8.34(d, 2H); 8.11(bs, 1H); 7.40(d, 4H); 7.49(m, 4H); 7.20 (m, 4H); 4.22(s, 1H); 3.42(m, 4H); 2.24–2.47 (m, 8H); 1.39–1.60(m, 4H) | | | (M + 23) |
| 104 | SBR-11-3539 | N-(2-(4-Benzyl-piperidin-1-yl)-ethyl)-N'-cyano-N"-pyridin-4-yl-guanidine | (CDC$_{13}$, ppm): 8.49(dd, 2H); 7.33–7.20(m, 5H); 7.12(dd, 2H); 6.41(s, 1H); 3.52–3.43(m, 2H); 3.05(dd, 2H); 2.66–2.57 (m, 4H); 2.18(app t, 2H); 1.76–1.66(m, 2H); 1.36–1.27(m, 3H) | 362.2 | 363.2 | |
| 105 | SBR-11-3775 | N-(3-(4-Benzyl-piperidin-1-yl)-propyl)-N'-methyl-N"-pyridin-4-yl-guanidine | (CDC$_{13}$, ppm): 8.60(dd, 2H); 7.33–7.10(m, 7H); 4.23(dd, 1H); 3.51(dd, 2H); 2.93(dd, 2H); 2.59–2.37(m, 4H); 1.97–1.20 (m, 9H) | 376.24 | 377.2 | |
| 106 | SBR-11-4089 | 5-Dimethylamino-naphthalene-1-sulfonic acid (4-(N"-pyridin-4-yl-guanidinomethyl)-3-methyl-phenyl)-amide | (DMSO-d$_6$, ppm): 9.82 (bs. 1H); 8.36(m, 3H); 8.26(t, 1H); 7.97(d, 1H); 7.55(m, 2H); 7.23(d, 2H); 7.16(d, 2H); 6.98(d, 1H); 6.89(d, 1H); 4.35 (d, 2H); 2.82(s, 6H); 1.89 (s, 3H); | 513.19 | 514.1 | |
| 107 | SBR-11-4084 | N-(1-(5-Dimethylamino-naphthalene-1-sulfonyl) 1H-indazol-5-yl)-N'-cyano-N"-pyridin-4-yl-guanidine | (DMSO-d$_6$, ppm): 10.0 (bs, 1H); 9.34(s, 1H); 8.61(t, 2H); 8.33(s, 2H); 8.22(d, 1H); 7.79(t, 1H); 7.71(s, 1H); 7.56(m, 2H); 7.31(d, 1H); 7.20 (d, 2H); 2.76(s, 6H); | 510.57 | 511.1 | |
| 108 | SBR-11-3940 | 5-Dimethylamino-naphthalene-1-sulfonic acid (4-(N'-cyano-N"-pyridin-3-yl-guanidinomethyl)-phenyl)-amide | (DMSO-d$_6$, ppm): 10.64 (bs, 1H), 9.15(bs, 1H), 8.42(mt, 3H), 8.33(m, 1H), 8.20(d, 1H), 7.73 (bs, 1H), 7.59(m, 3H), 7.33(m, 1H), 7.23(d, 1H), 7.08(d, 2H), 7.01 (d, 2H), 4.27(d, 2H), 2.83(s, 6H) | 499.18 | 500.3 | 522.1 (M + 23) |
| 109 | SBR-11-3939 | Naphthalene-1-sulfonic acid (4-(N'-cyano-N"-pyridin-3-yl-guanidinomethyl)-phenyl)-amide | (DMSO-d$_6$, ppm): 10.65 (bs, 1H), 9.15(bs, 1H), 8.73(d, 1H), 8.40(s, 1H), 8.34(d, 1H), 8.20(d, 2H), 8.06(d, 1H), 7.65 (m, 5H), 7.34(m, 1H), 7.07(d, 2H), 6.98(d, 2H), 4.24(d, 2H) | 456.14 | 457.2 | 479.1 (M + 23) |
| 110 | SBR-11-4096 | 5-Dimethylamino-naphthalene-1-sulfonic acid (4-(N'-cyano-N"-pyridin-4-yl-guanidinomethyl)-2-methyl-phenyl)-amide | (CDCl$_3$ ppm): 8.43(dd, 3H); 8.29(d, 1H); 8.12 (dd, 1H); 7.54(dd, 1H); 7.37(m, 2H); 7.13(d, 1H); 7.03(dd, 2H); 6.70 (dd, 1H); 6.60(d, 1H); 4.34(d, 2H); 3.42(s, 3H); 2.82(s, 6H) | 529.19 | 530.1 | |
| 111 | SBR-11-2733 | N-[4-(4-Benzhydryl-piperazin-1-yl)-butyl]-N'-cyano-N"-pyridin-4-yl-guanidine | (DMSO-d$_6$, ppm): 9.71 (bs, 1H), 8.34(d, 2H), 8.11(bs, 1H), 7.40(m, 4H), 7.13–7.36(m, 8H), 4.22(s, 1H); 3.42(m, 2H), 2.24–2.47(m, 8H), 1.39–1.60(m, 4H) | 467.28 | 468.3 | 490.3 (M + 23) |
| 112 | SBR-11-4149 | N-[2-(4-Benzhydrylidene-piperidin-1-yl)-ethyl]-N'-cyano-N"-pyridin-4-yl-guanidine | (CD$_3$OD, ppm): 8.39(d, 2H), 7.42(d, 2H), 7.09–7.29(m, 10H), 3.51(t, 2H), 2.64(m, 6H), 2.41 (m, 4H) | 436.24 | 437.4 | 459.2 (M + 23) |
| 113 | SBR-11-4344 | 4-[(Bis-naphthalen-1-ylmethyl-amino)- | (DMSO-d$_6$, ppm): 10.05 (bs, 1H), 8.10(b, 2H), | 538.28 | 539.5 | 561.4 (M + 23) |

-continued

| Example | Compound ID | Name | NMR | Mass (Cald) | M + 1 | Mass(other) |
|---|---|---|---|---|---|---|
| | | methyl]-N-cyano-N'-pyridin-4-yl-piperidine-1-carboxamidine | 7.82–7.93(m, 6H), 7.54 (d, 2H), 7.45(m, 4H), 7.22(t, 2H), 6.63(b, 2H), 3.99(s, 4H), 3.72(d, 2H), 2.83(t, 2H), 2.37(d, 2H), 1.92(m, 1H), 1.60(d, 2H), 0.64(m, 2H) | | | |
| 114 | SBR-11-4407 | N-{2-[4-(10,11-Dihydro-5H-dibenzo[a,d]cyclohepten-5-yl)-piperazin-1-yl]-ethyl}-N'-cyano-N"-pyridin-4-yl-guanidine | (CD₃OD, ppm): 8.40(d, 2H), 7.18–7.43(m, 10H), 4.30(s, 1H), 3.47–3.60 (m, 4H), 3.45(t, 2H), 2.45–2.61(m, 10H) | 465.26 | 466.3 | |
| 115 | SBR-11-4410 | N-{2-[4-(2,2-Diphenyl-ethyl)-piperazin-1-yl]-ethyl}-N'-cyano-N"-pyridin-4-yl-guanidine | (CD₃OD, ppm): 8.38(d, 2H), 7.40(d, 2H), 7.14–7.29(m, 10H), 4.22(t, 1H), 3.46(t, 2H), 3.03(d, 2H), 2.50–2.60(m, 10H) | 453.26 | 454.5 | 476.3 (M + 23) |
| 116 | SBR-11-4482 | N-{2-[4-(4-Chloro-phenoxy)-piperidin-1-yl]-ethyl}-N'-cyano-N"-pyridin-4-yl-guanidine | (CD₃OD, ppm): 8.40(d, 2H), 7.42(d, 2H), 7.25(d, 2H), 6.92(d, 2H), 4.46 (m, 1H), 3.55(t, 2H), 2.92 (m, 2H), 2.73(t, 2H), 2.60 (m, 2H), 2.04(m, 2H), 1.85(m, 2H) | 398.16 | 399.2 | 421.2 (M + 23) |
| 117 | SBR-11-4488 | N-[3-(4-Benzhydryloxy-piperidin-1-yl)-propyl]-N'-cyano-N"-pyridin-4-yl-guanidine | (CD₃OD, ppm): 8.36(d, 2H), 7.18–7.50(m, 12H), 5.56(s, 1H), 3.52(m, 1H), 3.42(t, 2H), 2.76(m, 2H), 2.43(t, 2H), 2.21(m, 2H), 1.85(m, 2H), 1.80(m, 2H), 1.70(m, 2H) | 468.26 | 469.4 | |
| 118 | SBR-11-4490 | 4-(N'-Cyano-N"-pyridin-4-yl-guanidinomethyl)-piperidine-1-carboxylic acid diphenylamide | (CD₃OD, ppm): 8.51(d, 2H), 7.63(bs, 2H), 6.95–7.40(m, 10H), 4.04(d, 2H), 3.34((m, 2H), 2.75 (m, 2H), 1.83(m, 2H), 1.66(m, 2H), 1.11(m, 2H) | 453.23 | 454.2 | 476.2 (M + 23) |
| 119 | SBR-11-4496 | N-Cyano-N'-pyridin-4-yl-N"-[2-(2-p-tolyloxy-ethylsulfanyl)-ethyl]-guanidine | (DMSO-d₆, ppm): 9.55(br s, 1H), 8.38(d, 2H), 7.88 (br s, 1H), 7.25(d, 2H), 7.08(d, 2H), 6.83(d, 2H), 4.10(t, 2H), 3.48(t, 3H), 2.90(t, 2H), 2.80(t, 2H). | 355.15 | | 378.1 (M + 23) |
| 120 | SBR-11-4497 | N-{2-[4-(2-Benzhydryloxy-ethyl)-piperidin-1-yl]ethyl}-N'-cyano-N"-pyridin-4-yl-guanidine | (CD₃OD, ppm): 8.30(d, 2H), 7.38(d, 2H), 7.15–7.30(m, 10H), 5.32(s, 1H), 3.50(m, 2H), 3.41(t, 2H), 2.98(m, 2H), 2.78 (m, 1H), 2.58(m, 2H), 1.98(m, 1H), 1.56(m, 7H) | 482.28 | 483.4 | 505.4 (M + 23) |
| 121 | SBR-11-4499 | N-[4-(4-Benzhydryloxy-piperidin-1-yl)-butyl]-N'-cyano-N"-pyridin-4-yl-guanidine | (CD₃OD, ppm): 8.51(d, 2H), 7.70(bs, 2H), 7.18–7.45(m, 10H), 5.60(s, 1H), 3.55(t, 2H), 3.42(m, 1H), 3.15(m, 2H), 2.95 (m, 1H), 2.15(m, 1H), 1.72(m, 11H) | 482.28 | 483.3 | 505.3 (M + 23) |
| 122 | SBR-11-4500 | N-[4-(4-Benzhydryloxy-piperidin-1-yl)-butyl]-N'-cyano-N"-pyridin-3-yl-guanidine | (CD₃OD, ppm): 8.50(s, 1H), 8.40(d, 1H), 7.80(d, 1H), 7.15–7.55(m, 11H), 5.60(s, 1H), 3.54(t, 2H), 3.42(m, 1H), 3.14(m, 2H), 2.96(m, 1H), 2.14 (m, 1H), 1.70(m, 11H) | 482.28 | 483.3 | 505.3 (M + 23) |
| 123 | SBR-11-4531 | N-(2-{4-[(4-Chloro-phenyl)-phenyl-methoxy]-piperidin-1-yl}-ethyl)-N'-cyano-N"-pyridin-4-yl-guanidine | (CD₃OD, ppm): 8.39(d, 2H), 7.20–7.50(m, 11H), 5.59(s, 1H), 3.52(m, 1H), 3.48(t, 2H), 2.86(m, 2H), 2.60(t, 2H), 2.32(m, 2H), 1.91(m, 2H), 1.73(m, 2H) | 488.21 | 489.3 | 511.3 (M + 23) |

-continued

| Example | Compound ID | Name | NMR | Mass (Cald) | M + 1 | Mass(other) |
|---|---|---|---|---|---|---|
| 124 | SBR-11-4532 | N-(3-{4-[(4-Chloro-phenyl)-phenyl-methoxy]-piperidin-1-yl}-propyl)-N'-cyano-N"-pyridin-4-yl-guanidine | (CD$_3$OD, ppm): 8.38(d, 2H), 7.20–7.50(m, 11H), 5.56(s, 1H), 3.50(m, 1H), 3.45(t, 2H), 2.78(m, 2H), 2.46(t, 2H), 2.27(m, 2H), 1.85(m, 2H), 1.81(m, 2H), 1.71(m, 2H) | 502.22 | 503.2 | 525.2 (M + 23) |
| 125 | SBR-11-4533 | N-(4-{4-[(4-Chloro-phenyl)-phenyl-methoxy]-piperidin-1-yl}-butyl)-N'-cyano-N"-pyridin-4-yl-guanidine | (CD$_3$OD, ppm): 8.36(d, 2H), 7.20–7.45(m, 11H), 5.58(s, 1H), 3.49(m, 1H), 3.38(t, 2H), 2.81(m, 2H), 2.43(t, 2H), 2.28(m, 2H), 1.90(m, 2H), 1.73(m, 2H), 1.61(m, 4H) | 516.24 | 517.3 | 539.2 (M + 23) |
| 126 | SBR-11-4537 | N-Cyano-N'-{2-[4-(phenyl-p-tolyl-methoxy)-piperidin-1-yl]-ethyl}-N"-pyridin-4-yl-guanidine | (CD$_3$OD, ppm): 8.38(d, 2H), 7.10–7.50(m, 11H), 5.56(s, 1H), 3.55(m, 1H), 3.50(t, 2H), 2.90(m, 2H), 2.65(t, 2H), 2.36(m, 2H), 2.30(s, 3H), 1.92(m, 2H), 1.75(m, 2H) | 468.26 | 469.4 | 491.3 (M + 23) |
| 127 | SBR-11-4538 | N-Cyano-N'-{3-[4-(phenyl-p-tolyl-methoxy)-piperidin-1-yl]-propyl}-N"-pyridin-4-yl-guanidine | (CD$_3$OD, ppm): 8.36(d, 2H), 7.08–7.45(m, 11H), 5.51(s, 1H), 3.45(m, 1H), 3.41(t, 2H), 2.76(m, 2H), 2.45(t, 2H), 2.28(s, 3H), 2.21(m, 2H), 1.86(m, 2H), 1.79(m, 2H), 1.69(m, 2H) | 482.28 | 483.4 | 505.4 (M + 23) |
| 128 | SBR-11-4539 | N-Cyano-N'-{4-[4-(phenyl-p-tolyl-methoxy)-piperidin-1-yl]-butyl}-N"-pyridin-4-yl-guanidine | (CD$_3$OD, ppm): 8.36(d, 2H), 7.05–7.45(m, 11H), 5.53(s, 1H), 3.49(m, 1H), 3.39(t, 2H), 2.79(m, 2H), 2.41(t, 2H), 2.29(s, 3H), 2.22(m, 2H), 1.90(m, 2H), 1.70(m, 2H), 1.60(m, 4H) | 496.3 | 497.4 | 519.4 (M + 23) |
| 129 | SBR-11-4541 | N-[3-(4-Benzhydryloxymethyl-piperidin-1-yl)-propyl]-N'-cyano-N"-pyridin-4-yl-guanidine | (CD$_3$OD, ppm): 8.32(d, 2H), 7.15–7.55(m, 12H), 5.33(s, 1H), 3.42(t, 2H), 3.26(d, 2H), 2.95(d, 2H), 2.43(t, 2H), 1.98(m, 2H), 1.80(m, 2H), 1.71(d, 2H), 1.65(m, 1H), 1.32(m, 2H) | 482.28 | 483.4 | 505.3 (M + 23) |
| 130 | SBR-11-4542 | N-[4-(4-Benzhydryloxymethyl-piperidin-1-yl)-butyl]-N'-cyano-N"-pyridin-4-yl-guanidine | (CD$_3$OD, ppm): 8.36(d, 2H), 7.15–7.45(m, 12H), 5.34(s, 1H), 3.40(t, 2H), 3.29(d, 2H), 3.00(d, 2H), 2.43(t, 2H), 2.07(m, 2H), 1.78(d, 2H), 1.70(m, 1H), 1.61(m, 4H), 1.38(m, 2H) | 496.3 | 497.4 | 519.3 (M + 23) |
| 131 | SBR-11-4545 | N-(2-{4-[Bis-(4-chloro-phenyl)-methoxy]-piperidin-1-yl}-ethyl)-N'-cyano-N"-pyridin-4-yl-guanidine | (CD$_3$OD, ppm): 8.38(d, 2H), 7.40(d, 2H), 7.32(m, 8H), 5.59(s, 1H), 3.55(m, 1H), 3.48(t, 2H), 2.85(m, 2H), 2.60(t, 2H), 2.33(m, 2H), 1.91(m, 2H), 1.73(m, 2H) | 522.17 | 523.2 | 545.1 (M + 23) |
| 132 | SBR-11-4546 | N-(3-{4-[Bis-(4-chloro-phenyl)-methoxy]-piperidin-1-yl}-propyl)-N'-cyano-N"-pyridin-4-yl-guanidine | (CD$_3$OD, ppm): 8.37(d, 2H), 7.25–7.40(m, 10H), 5.56(s, 1H), 3.48(m, 1H), 3.43(t, 2H), 2.76(m, 2H), 2.45(t, 2H), 2.22(m, 2H), 1.88(m, 2H), 1.80(m, 2H), 1.68(m, 2H) | 536.19 | 536.9 | 559.0 (M + 23) |
| 133 | SBR-11-4547 | N-(4-{4-[Bis-(4-chloro-phenyl)-methoxy]-piperidin-1-yl}-butyl)-N'-cyano-N"-pyridin-4-yl-guanidine | (CD$_3$OD, ppm): 8.37(d, 2H), 7.25-7.40(m, 10H), 5.58(s, 1H), 3.46(m, 2H), 3.39(t, 2H), 2.79(m, 2H), 2.41(t, 2H), 2.25(m, 2H), 1.89(m, 2H), 1.70(m, 2H), 1.60(m, 4H) | 550.2 | 551 | 573.1 (M + 23) |
| 134 | SBR-11-4561 | N-(2-{4-[Bis-(4-chloro-phenyl)- | (CD$_3$OD, ppm): 8.30(d, 2H), 7.46(d, 2H), 7.05 | 536.19 | 537.1 | 558.7 (M + 23) |

-continued

| Example | Compound ID | Name | NMR | Mass (Cald) | M + 1 | Mass(other) |
|---|---|---|---|---|---|---|
| | | methoxymethyl]-piperidin-1-yl}-ethyl)-N'-cyano-N"-pyridin-4-yl-guanidine | (m, 8H), 5.11(s, 1H), 3.67 (t, 2H), 3.48(m, 2H), 3.20 (m, 2H), 3.07(m, 2H), 2.80(m, 2H), 1.75(m, 3H), 1.45(m, 2H) | | | |
| 135 | SBR-11-4562 | N-(3-{4-[Bis-(4-chloro-phenyl)-methoxymethyl]-piperidin-1-yl}-propyl)-N'-cyano-N"-pyridin-4-yl-guanidine | (CD$_3$OD, ppm): 8.33(d, 2H), 7.36(d, 2H), 7.30 (m, 8H), 5.32(s, 1H), 3.43 (t, 2H), 3.24(d, 2H), 2.95 (d, 2H), 2.44(t, 2H), 1.98 (m, 2H), 1.83(m, 2H), 1.71(m, 2H), 1.65(m, 1H), 1.33(m, 2H) | 550.2 | 550.9 | 573.1 (M + 23) |
| 136 | SBR-11-4563 | N-(4-{4-[Bis-(4-chloro-phenyl)-methoxymethyl]-piperidin-1-yl}-butyl)-N'-cyano-N"-pyridin-4-yl-guanidine | (CD$_3$OD, ppm): 8.36(d, 2H), 7.30(m, 10H), 5.32 (s, 1H), 3.40(t, 2H), 3.26 (d, 2H), 2.95(d, 2H), 2.38 (t, 2H), 1.99(m, 2H), 1.74 (m, 2H), 1.60(m, 5H), 1.35(m, 2H) | 564.22 | 565 | |
| 137 | SBR-11-4570 | N-(2-{4-[Bis-(4-fluoro-phenyl)-methoxy]-piperidin-1-yl}-ethyl)-N'-cyano-N"-pyridin-4-yl-guanidine | (CD$_3$OD, ppm): 8.55(d, 2H), 7.70(d, 2H), 7.40 (m, 4H), 7.06(m, 4H), 5.64(s, 1H), 3.60(m, 1H), 3.50(t, 2H), 2.90(m, 2H), 2.62(t, 2H), 2.35(m, 2H), 1.98(m, 2H), 1.75(m, 2H) | 490.23 | 491.2 | |
| 138 | SBR-11-4624 | N-(2-{4-[(4-Chloro-phenyl)-phenyl-methyl]-piperazin-1-yl}-ethyl)-N'-cyano-N"-pyridin-4-yl-guanidine | (CD$_3$OD, ppm): 8.38(d, 2H), 7.15–7.45(m, 11H), 4.32(s, 1H), 3.48(t, 2H), 2.62(m, 6H), 2.45(m, 4H) | 473.21 | 474.2 | 496.2 (M + 23) |
| 139 | SBR-11-4625 | N-(3-{4-[(4-Chloro-phenyl)-phenyl-methyl]-piperazin-1-yl}-propyl)-N'-cyano-N"-pyridin-4-yl-guanidine | (CD$_3$OD, ppm): 8.39(d, 2H), 7.20–7.45(m, 11H), 4.22(s, 1H), 3.43(t, 2H), 2.47(m, 10H), 1.80(m, 2H) | 487.23 | 488.2 | 510.2 (M + 23) |
| 140 | SBR-11-4626 | N-(4-{4-[(4-Chloro-phenyl)-phenyl-methyl]-piperazin-1-yl}-butyl)-N'-cyano-N"-pyridin-4-yl-guanidine | (CD$_3$OD, ppm): 8.36(d, 2H), 7.10–7.45(m, 11H), 4.24(s, 1H), 3.39(t, 2H), 2.58(m, 4H), 2.46(m, 6H), 1.61(m, 4H) | 501.24 | 502.2 | 524.2 (M + 23) |
| 141 | SBR-11-4633 | N-[2-(4-Benzyl-piperazin-1-yl)-ethyl]-N'-cyano-N"-pyridin-4-yl-guanidine | (CD$_3$OD, ppm): 8.56(d, 2H), 7.51(m, 7H), 3.51(s, 2H), 3.43(t, 2H), 2.55(m, 10H) | 363.22 | 364.2 | 386.1 (M + 23) |
| 142 | SBR-11-4634 | N-[2-(4-Benzo[1,3]dioxol-5-ylmethyl-piperazin-1-yl)-ethyl]-N'-cyano-N"-pyridin-4-yl-guanidine | (CD$_3$OD, ppm): 8.37(d, 2H), 7.40(d, 2H), 6.84(s, 1H), 6.76(s, 2H), 5.93(s, 2H), 3.51(t, 2H), 3.48(s, 2H), 2.62(m, 10H) | 407.21 | 408.2 | 430.2 (M + 23) |
| 143 | SBR-11-4638 | N-[3-(4-Benzyl-piperazin-1-yl)-propyl]-N'-cyano-N"-pyridin-4-yl-guanidine | (CD$_3$OD, ppm): 8.38(d, 2H), 7.35(d, 2H), 7.31 (m, 5H), 3.54(s, 2H), 3.45 (t, 2H), 2.55(m, 8H), 2.50 (t, 2H), 1.82(m, 2H) | 377.23 | 378.2 | 400.2 (M + 23) |
| 144 | SBR-11-4639 | N-[3-(4-Benzo[1,3]dioxol-5-ylmethyl-piperazin-1-yl)-propyl]-N'-cyano-N"-pyridin-4-yl-guanidine | (CD$_3$OD, ppm): 8.39(d, 2H), 7.38(d, 2H), 6.83(s, 1H), 6.75(s, 2H), 5.92(s, 2H), 3.47(t, 2H), 3.44(s, 2H), 2.47(m, 10H), 1.81 (m, 2H) | 421.22 | 422.2 | 444.2 (M + 23) |
| 145 | SBR-11-4419 | N-[2-(2-Benzhydryl-oxyethoxy)ethyl]-N'-cyano-N"-pyridin-4-yl-guanidine | (CDCl$_3$, ppm): 8.15(d, 2H), 7.23–7.44(m, 13H), 7.05(br s, 1H), 5.36(s, 1H), 3.61–3.82(m, 8H) | 415.2 | 416.4 | 438.3 (M + 23) |
| 146 | SBR-11-4438 | 3-{2-[2-(N'-cyano-N"-pyridin-4-yl-guanidino)-ethoxy]-ethyl}-1,1-diphenyl- | (CD$_3$OD, ppm): 8.27(d, 2H), 7.72(m, 4H), 7.25 (d, 2H), 3.89(t, 2H), 3.84 (t, 2H), 3.71(t, 2H), 3.52 | 378.1 | 379.3 | 401.3 (M + 23) |

-continued

| Example | Compound ID | Name | NMR | Mass (Cald) | M + 1 | Mass(other) |
|---|---|---|---|---|---|---|
| 147 | SBR-11-4442 | urea N-{2-[2-(4-Methoxy-benzylsulfanyl)-ethoxy]-ethyl}-N'-cyano-N"-pyridin-4-yl-guanidine | (t, 2H) (CDCl$_3$, ppm): 8.44(d, 2H), 7.46(d, 2H), 7.19 (d, 2H), 7.02(br s, 1H), 6.85(br s, 1H), 6.84(d, 2H), 3.79(s, 3H), 3.55–3.82(m, 8H), 2.67(t, 2H) | 385.16 | 386.2 | 408.2 (M + 23) |
| 148 | SBR-11-4439 | Naphthalene-1-sulfonic acid {2-[2-(N'-cyano-N"-pyridin-4-yl-guanidino)-ethoxy]-ethyl}-amide | (CD$_3$OD, ppm): 8.68(d, 1H), 8.33(d, 2H), 8.22 (d, 1H), 8.15(d, 1H), 8.00(d, 1H), 7.58(m, 3H), 7.30(d, 2H), 3.41(t, 2H), 3.37(m, 4H), 3.09 (t, 2H) | 438.15 | 439.3 | 461.3 |

EXAMPLE 149

In vitro efficacy studies

In the primary screening, the test compounds were applied to a panel of five human cell lines at a concentration of 12.5 μM. From the results obtained from this primary screening, cytotoxic compounds were selected to apply to a panel of 27 cell lines at a range of different concentrations in the secondary screening. The concentration of a test compound that produces a cytotoxicity level of 50% (IC$_{50}$) was determined.

In the primary screening, clonogenic assay was used. Cells were seeded at a low cell density in 96 well flat-bottom plates and incubated for 24 hours at 37° C. in a 7% CO$_2$ atmosphere. The 5 cell lines used were: CX-1 (colon carcinoma), MDA-MB-435 (breast carcinoma), PC-3 (prostate carcinoma), H2 (leukemia), and CCD-39sk (normal skin fibroblasts). Test compounds at 12.5 μM were then added in duplicate to the cell plates and incubated for 6 days under the same conditions. MTS colorimetric assay (Promega), which measures cell viability based on the cellular conversion of a tetrazolium salt, was performed is directly in the 96 well plates at the end of the 6-day period. After the plates were read and recorded, viable adherent cells were stained with Crystal violet (Sigma) to verify the results obtained from the MTS assay.

In the secondary screening, IC$_{50}$ values were determined. Cells were seeded at a low cell density in 96 well flat-bottom plates and incubated for 24 hours at 37° C. in a 7% CO$_2$ atmosphere. Cell lines used in this screening were: CX-1 (colon carcinoma), MIP-101 (colon carcinoma), HCT-116 (colon carcinoma), HCT-29 (colon carcinoma), HCT-15 (colon carcinoma), MDA-MB-435 (breast carcinoma), MCF-7 (breast carcinoma), PC-3 (prostate carcinoma), DU-145 (prostate carcinoma), H2 (leukemia), K562 (leukemia), HL-60 (leukemia), RL (non-Hodgkin's B cell lymphoma), A549 (lung carcinoma), H510A (small cell lung carcinoma), ME-180 (cervical carcinoma), HeLa (cervical carcinoma), 2008 (cervical carcinoma), C13 (cervical carcinoma, CDDP resistant), ES-2 (ovarian carcinoma), MIA PaCa2 (pancreatic carcinoma), ACHN (renal adenocarcinoma), HepG2 (liver carcinoma), LOX (melanoma), G3361 (melanoma), CCD-39sk (normal skin fibroblasts), and CV-1 (transformed monkey kidney cells). Test compounds were added in duplicate in serial dilution from 0.005 to 10.0 μM to the cell plates. The cell plates were then incubated for 6 days under the same conditions. MTS assay was performed followed by staining of viable adherent cells with Crystal violet after the 6-day period. The results obtained from Crystal violet stained plates were used to compare and verify those obtained from the MTS assay.

Seventy of the one hundred thirty eight cyanoguanidine compounds tested were shown to have an IC$_{50}$ value of less than 5 μM towards RL (non-Hodgkin's lymphoma) cells, and five compounds demonstrated an IC$_{50}$ value of less than 0.005 μM. For CX-1 (colon carcinoma) cells, twenty four compounds tested were shown to have an IC$_{50}$ values of less than 5 μM and the IC$_{50}$ values of nine compounds were less than 0.005 μM. For DU-145 (prostate carcinoma) cells, sixteen compounds were shown to have an IC$_{50}$ value of less than 5 μM and two compounds demonstrated an IC$_{50}$ value less than 0.005 μM.

Several test compounds were shown to selectively target tumor cells in comparison to normal cells. For example, when comparing the IC$_{50}$ values obtained from using a normal cell line (CV-1) with those obtained from using a tumor cell line (PC-3), twenty cyanoguanidine compounds were shown to have a >50-fold selectivity of tumor cells and six compounds unexpectedly demonstrated a selectivity of 1000-fold or more. For comparison, Taxol and Etoposide (VP-16), two compounds that are currently in clinical use, demonstrated only a 20-fold and 0-fold selectivity, respectively.

EXAMPLE 150

In vivo Efficacy Studies

From the in vitro results obtained, cyanoguanidine compounds were selected for human tumor xenograft regression assays. Animals bearing established tumors (RL) were treated with a test compound for a three-week period. The growth of the tumors and the general health of the animals were monitored during the treatment and for an additional two weeks after dosing had been terminated to determine if tumor regrowth took place.

Non-Hodgkin's B cell lymphoma (RL) tumor cells, which were adapted to grow as solid tumors, were implanted by an intradermal injection of a tumor cell suspension (30×10$^6$ cells in 0. 1 mL media) in the flanks of female NIH Swiss nude mice (Taconic Labs). Each mouse was implanted with one tumor and 6–8 mice per group were used.

Dosing was initiated one week after implantation (Day 1), when tumors reached approximately 50 to 100 mm$^3$ in volume, with a test compound or vehicle five times per week for three weeks either intravenously (IV) or intraperitoneally (IP). Cyclophosphamide (CTX, Sigma) was used as a standard in the assays. Compounds were first dissolved in DMSO (Sigma) and formulated with 20% Cremophor RH40 (BASF) to a final concentration of 10% DMSO/18% Cremophor. The formulated solution was made fresh daily.

Tumors, assumed to be hemi-ellipsoid in shape, were measured with calipers in three dimensions. Tumor volumes were calculated using the equation:

$$\text{Volume} = 112 \, (L/2 \times W12 \times H) \, 4/3 \, \pi$$

where L=length, W=width, and H=height of the tumor. Animals were weighed and their general health was monitored during the course of the assay. When tumors became necrotic or if animals became moribund, the animals were euthanized by $CO_2$ asphyxiation. Student's t test was used to determine if there was a significant difference between the data obtained in the compound treated group and the vehicle treated group.

In a preliminary RL tumor growth regression assay, eight compounds were administered twice a day (via IV route in the morning and IP route in the afternoon) for five days per week for a three-week period. Five of the eight compounds completely regressed all tumors within the first two weeks of the dosing period. Four of these compounds, SBR-11-2780 (75 mg/kg), SBR-11-2889 (90 mg/kg), SBR-11-2897 (75 mg/kg), SBR-11-2900 (60 mg/kg), showed little gross toxicity and the animals receiving the compounds had less than 10% weight loss. One compound, SBR-11-2727 (60 mg/kg), showed signs of gross toxicity within the first week and dosing was reduced to once per day. For comparison, cyclophosphamide, reduced the average tumor volume to 2% of control by Day 18. The remaining three compounds also demonstrated efficacy in the RL tumor xenograph model. Compounds SBR-11-2899 (75 mg/kg), SBR-11-2750 (75 mg/kg), and SBR-11-2749 (75 mg/kg) reduced the average tumor volume to 10%, 14%, and 18% of the tumor volume obtained in the control on Day 21, respectively. One compound, SBR-11-4483 (60 mg/kg) was administered once per day (via IV route) for a two-week period. By day 19, a reduction of the average tumor volume to 1% was observed. The test animals showed less than 10% weight loss. All compounds tested were able to significantly reduce tumor volumes in comparison to the results obtained in the vehicle treated controls ($p<0.05$).

The ability of compounds to act in a dose dependent manner was assayed in an RL tumor growth regression assay using compounds SBR-11-2897 and SBR-11-2780. SBR-11-2780 demonstrated a dose dependent effect: tumor volumes were reduced to 86%, 24%, and 3% of the average tumor volumes obtained in the control group with doses of 20, 40, and 80 mg/kg, respectively. All three doses of SBR-11-2897 resulted in an almost complete reduction of average tumor volumes relative to vehicle treated controls (4 to 6% of control). Less than 10% weight loss was observed for all mice except for one mouse from the CTX-treated group.

EXAMPLE 151

Acute Toxicity Studies

Female SW mice with body weights over 20 g were used in the acute toxicity study. The mice were divided into three groups: untreated, treated with vehicle, and treated with a test cyanoguanidine compound. Three mice were assigned to each group and were given doses by a single intravenous bolus administration. The highest doses tested produced acute lethal or significantly toxic effects. The experiment lasted for one week. The mortality, clinical signs of toxicity, and body weight of each animal were monitored and recorded every day or every other day. Necropsy and gross examinations of major organs were performed on the animals which died during the study as well as those sacrificed at the end of the experiment. Histopathogical evaluations were conducted on 2–3 Hematoxylin and Eosin stained tissue sections from major organs including the heart, liver, kidneys, lungs and spleen, of the animals which died or were treated with the highest dose of the test compound.

The lethal doses of the compounds shown in Examples 1–148 above, which is defined as causing 1/3 animal deaths, were determined to be about 150 to about 200 mg/kg. SBR-11-2897 and SBR-11-4483 were each administered to three animals at the doses of 200, 150, and 100 mg/kg, respectively. All animals survived.

EXAMPLE 152

Preliminary Sub-acute Toxicity Studies

The preliminary sub-acute toxicity study was carried out in parallel on the same animals used in the efficacy study (see Example 150). After continuous treatment for 3 weeks with repeated intravenous and intraperitoneal dosing, three out of eight animals were sacrificed in each treatment group. The remaining animals were sacrificed two weeks later. Necropsy, liver weight, gross examinations of visible abnormalities in the major organs, and limited histological studies were conducted in all animals. In addition, blood chemistry tests and complete blood cell count analyses were performed in most of the animals.

In the sub-acute toxicity study, a repeated dosing of about 150 to 180 mg/kg/day (i.v.+i.p.) for 3 weeks was well tolerated by the animals. The toxicity observed in the animals treated with SBR-11-2897 at the total dose of 150 mg/kg/day (i.v.+i.p.) for 3 weeks included only a mild reduction of the total white blood cell count and increased blood AST (aspartate aminotransferase) and ALT (alanine aminotransferase) levels in 1/3 animals with a moderate reduction in the size of the white pulp in the spleen and very mild mononuclear cell aggregates in the liver. The toxicity observed in the animals treated with SBR-11-4483 at the total dose of 60 or 120 mg/kg/day (i.v.) for two weeks included dose-dependent behavioral changes, moderate dose-dependent decreases in body weight at the dose of 120 mg/kg, mild increases of blood ALT and AST levels, along with some histopathological changes such as mild lung congestion with mild inflammatory cell infiltrates at the does of 120 mg/kg, mild and focal mononuclear cell aggreates in the liver with a few degenerated/apototic hapatocytes at 60 mg/kg, and a small focal well-circumscribed necrosis with minimal inflammatory infiltrate in the liver at 120 mg/kg.

OTHER EMBODIMENT

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:
1. A compound of the following formula:

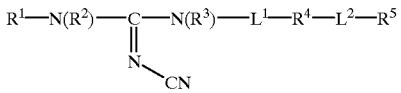

wherein
R$^1$ is 3-pyridyl, 4-pyridyl, or quinolinyl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, alkylcarbonyloxy, alkyloxycarbonyl, alkylcarbonyl, alkylcarbonylamino, aminocarbonyl, alkylsulfonylamino, aminosulfonyl, sulfonic acid, or alkylsulfonyl;

each of R$^2$ and R$^3$, independently, is hydrogen, alkyl, alkoxy, hydroxylalkyl, thioalkyl, aminoalkyl, cycloalkyl, heterocycloalkyl, aryl, heteroaryl, alkylcarbonyloxy, alkyloxycarbonyl, alkylcarbonyl, alkylcarbonylamino, or aminocarbonyl;

L$^1$ is —X$^1$—Y$^1$—X$^2$— in which each of X$_1$ and X$^2$, independently, is a bond, or a C$_{1-6}$ alkylene chain optionally containing a double bond or a triple bond and further optionally substituted with alkoxy, hydroxyl, halo, carboxyl, amino, nitro, cyano, cycloalkyl, heterocycloalkyl, aryl, heteroaryl, aminosulfonyl, alkylsulfonylamino, alkylcarbonyloxy, alkyloxycarbonyl, alkylcarbonyl, formyl, alkylcarbonylamino, or aminocarbonyl; and Y$^1$ is —O—, —S—, —SO—, —SO$_2$—, —N(R$^a$)—, —CO—, —N(R$^a$)—CO—, —CO—N(R$^a$)—, —N(R$^a$)—CO—CO—, —N(R$^a$)—SO$_2$—, —SO$_2$—N(R$^a$)—, —N(R$^a$)—CO—O—, —O—CO—N(R$^a$)—, —N(R$^a$)—CO—N(R$^b$)—, —N(R$^a$)—CS—N(R$^b$)—CO—, —CO—N(R$^a$)—CS—N(R$^b$)—, —O—CO—, —CO—O—, —O—SO$_2$—, —SO$_2$—O—, —O—S—CO—N(R$^a$)—, —N(R$^a$)—CO—S—O—, —O—CO—O—, —CO—N(R$^a$)—S—CO—N(R$^b$)—, —N(R$^a$)—CO—S—N(R$^b$)—CO—, or a bond; each of R$^a$ and R$^b$, independently, being hydrogen, alkyl, alkoxy, hydroxylalkyl, hydroxyl, amino, nitro, cyano, halo, haloalkyl, cycloalkyl, heterocycloalkyl, aryl, heteroaryl, aralkyl, or heteroaralkyl;

R$^4$ is aryl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminioalkyl, nitro, cyano, aryloxy, heteroaryloxy, aralkyloxy, heteroaralkyloxy, alkylcarbonyloxy, alkyloxycarbonyl, alkylcarbonyl, formyl, oxo, alkylcarbonylamino, aminocarbonyl, alkylsulfonylamino, aminosulfonyl, sulfonic acid, or alkylsulfonyl;

L$^2$ is —X$^3$—Y$^2$—X$^4$— in which each of X$^3$ and X$^4$, independently, is a bond, or a C$_{1-6}$ alkylene chain optionally containing a double bond or a triple bond and further optionally substituted with alkoxy, hydroxyl, halo, carboxyl, amino, nitro, cyano, cycloalkyl, heterocycloalkyl, aryl, heteroaryl, aminosulfonyl, alkylsulfonylamino, alkylcarbonyloxy, alkyloxycarbonyl, alkylcarbonyl, formyl, alkylcarbonylamino, or aminocarbonyl; and Y$^2$ is —O—, —S—, —SO—, —SO$_2$—, —N(R$^c$), —CO—, —N(R$^c$)—CO—, —CO—N(R$^c$)—, —N(R$^c$)—CO—CO—, —N(R$^c$)—SO$_2$—, —SO$_2$—N(R$^c$)—, —N(R$^c$)—CO—O—, —O—CO—N(R$^c$)—, —N(R$^c$)—CO—N(R$^d$)—, —N(R$^c$)—CS—N(R$^d$)—CO—, —CO—N(R$^c$)—CS—N(R$^d$)—, —O—CO—, —CO—O—, —O—, SO$_2$—, —SO$_2$—O—, —O—S—CO—N(R$^c$)—, —N(R$^c$)—CO—S—O—, —O—CO—O—, —CO—N(R$^c$)—S—CO—N(R$^d$)—, —N(R$^c$)—CO—S—N(R$^d$)—CO— or a bond; each of R$^c$ and R$^d$, independently, being hydrogen, alkyl, alkoxy, hydroxylalkyl, hydroxyl, amino, nitro, cyano, halo, haloalkyl, cycloalkyl, heterocycloalkyl, aryl, heteroaryl, aralkyl, or heteroaralkyl; and R$^5$ is cycloalkyl, heterocycloalkyl, cycloalkenyl, heterocycloalkenyl, aryl, or heteroaryl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, nitro, cyano, aryloxy, heteroaryloxy, aralkoxy, heteroaralkoxy, alkylcarbonyloxy, alkyloxycarbonyl, arylcarbonyloxyalkyl, aryloxycarbonylalkyl, alkylcarbonyl, formyl, oxo, aminocarbonyl, alkylcarbonylamino, alkylsulfonylamino, aminosulfonyl, aminocarbonyloxy, or alkyloxycarbonylamino;

provided that each of Y$^1$ and Y$^2$ is not a bond simultaneously; and that when neither Y$^1$ nor Y$^2$ is a bond, at least one of X$^2$, R$^4$, and X$^3$ is not a bond;

or an N-oxide derivative or a salt thereof.

2. The compound of claim 1, wherein R$^1$ is unsubstituted 4-pyridyl.

3. The compound of claim 1, wherein each of R$^2$ and R$^3$, independently, is hydrogen.

4. The compound of claim 1, wherein Y$^1$ is —SO—, —SO$_2$—, —N(R$^a$)—CO—CO—, —N(R$^a$)—SO$_2$—, —SO$_2$—N(R$^a$)—, —N(R$^a$)—CO—N(R$^b$)—N(R$^a$)—CS—N(R$^b$)—CO—, —CO—N(R$^a$)—CS—N(R$^b$)—, —O—SO$_2$—, —SO$_2$—O—, —CO—N(R$^a$)—S—CO—N(R$^b$)—, —N(R$^a$)—CO—S—N(R$^b$)—CO—, or a bond.

5. The compound of claim 1, wherein Y$^2$ is —SO—, —SO$_2$—, —N(R$^a$)—CO—CO—, —N(R$^a$)—SO$_2$—, —SO$_2$—N(R$^a$)—, —N(R$^a$)—CO—N(R$^b$)—, —N(R$^a$)—CS—N(R$^b$)—CO—, —CO—N(R$^a$)—CS—N(R$^b$)—, —O—SO$_2$—, —SO$_2$—O—, —CO—N(R$^a$)—S—CO—N(R$^b$)—, —N(R$^a$)—CO—S—N(R$^b$)—CO—, or a bond.

6. The compound of claim 1, wherein neither one of Y$^1$ and Y$^2$ is a bond.

7. The compound of claim 6, wherein R$^5$ is phenyl or naphthyl, optionally substituted with alkyl, alkoxy, amino, or halo.

8. The compound of claim 7, wherein R$^1$ is unsubstituted 4-pyridyl, and each of R$^2$ and R$^3$, independently, is hydrogen.

9. The compound of claim 8, wherein X$^1$ is a C$_{1-4}$ alkylene chain, Y$^1$ is —O—, —S—, —O—CO—, —N(R$^a$)—, —N(R$^a$)—CO—, or —N(R$^a$)—CO—N(R$^b$)—, in which each of R$^a$ and R$^b$, independently, is alkyl, alkylcarbonyl, aryl, heteroaryl, aralkyl, or heteroaralkyl, and X$^2$ is a bond.

10. The compound of claim 9, wherein X$^3$ is a C$_{1-4}$ alkylene chain, Y$^2$ is —O—, —S—, —O—CO—, —N(R$^c$)—, —N(R$^c$)—CO—, or —N(R$^c$)—CO—N(R$^d$)—, in which each of R$^c$ and R$^d$, independently, is alkyl, alkylcarbonyl, aryl, heteroaryl, aralkyl, or heteroaralkyl, and X$^4$ is a bond or a C$_{1-2}$ alkylene chain optionally substituted with aryl, heteroaryl, aralkyl, or heteroaralkyl.

11. The compound of claim 1, wherein Y$^1$ is a bond.

12. The compound of claim 11, wherein X$^1$ is a C$_{1-2}$ alkylene chain, and X$^2$ is a bond or a C$_{1-2}$ alkylene chain.

13. The compound of claim 11, wherein $X^3$ is a bond or a $C_{1-4}$ alkylene chain optionally containing a double bond, $Y^2$ is —O—, —S—, —SO$_2$—, —N(R$^c$)—, —N(R$^c$)—CO—, —N(R$^c$)—CO—CO—, —N(R$^c$)—CO—O—, —N(R$^c$)—SO$_2$—, —N(R$^c$)—CS—N(R$^d$)—CO—, —N(R$^c$)—CO—S—N(R$^d$)—CO—, —N(R$^c$)—CO—S—O—, or —N(R$^c$)—CO—N(R$^d$)—, in which each of R$^c$ and R$^d$, independently, is alkyl, alkylcarbonyl, aryl, heteroaryl, aralkyl, or heteroaralkyl, and $X^4$ is a bond or a $C_{1-4}$ alkylene chain optionally substituted with aryl, heteroaryl, aralkyl, or heteroaralkyl.

14. The compound of claim 11, wherein $R^4$ is phenyl.

15. The compound of claim 11, wherein $R^5$ is aryl or heteroaryl.

16. The compound of claim 15, wherein $R^5$ is phenyl, naphthyl, indolyl, or chromanyl, optionally substituted with alkyl, aralkyl, alkylcarbonyloxy, alkyloxycarbonyl, alkoxy, amino, halo, or haloalkyl.

17. The compound of claim 16, wherein $R^1$ is unsubstituted 4-pyridyl, and each of $R^2$ and $R^3$, independently, is hydrogen.

18. The compound of claim 17, wherein $X^1$ is a $C_{1-2}$ alkylene chain, $Y^1$ is a bond, and $X^2$ is a bond or a $C_{1-2}$ alkylene chain.

19. The compound of claim 18, wherein $X^3$ is a bond or a $C_{1-2}$ alkylene chain optionally containing a double bond, $Y^2$ is —O—, —SO$_2$—, —N(R$^c$)—SO$_2$—, —N(R$^c$)—CO—, —N(R$^c$)—CO—N(R$^d$)—, or a bond, and $X^4$ is a bond or a $C_{1-2}$ alkylene chain optionally substituted with aryl, heteroaryl, aralkyl, or heteroaralkyl.

20. The compound of claim 19, wherein $R^5$ is phenyl or naphthyl, optionally substituted with alkyl, aralkyl, alkoxy, amino, halo, or haloalkyl.

21. The compound of claim 20, wherein $R^4$ is phenyl, $X^3$ is a bond, and $Y^2$ is —N(R$^c$)—CO— or —N(R$^c$)—SO$_2$—.

22. The compound of claim 21, where the compound is 5-dimethylamino-naphthalene-1-sulfonic acid (4-(N'-cyano-"-pyridin-4-yl-guanidinomethyl)-phenyl)-amide, naphthalene-1-sulfonic acid (4-(N'-cyano-N"-pyridin-4-yl-guanidinomethyl)-phenyl)-amide, N-(4-(N'-cyano-N"-pyridin-4-yl-guanidino-methyl)-phenyl)-3-trifluoromethyl-benzenesulfonamide, 2,4,6-trimethyl-N-(4-(N'-cyano-N"-pyridin-4-yl-guani-dinomethyl)-phenyl)-benzenesulfonamide, or 4-chloro-N-(4-(N'-cyano-N"-pyridin-4-yl-guanidinomethyl)-phenyl)-benzenesulfonamide.

23. A compound of the following formula:

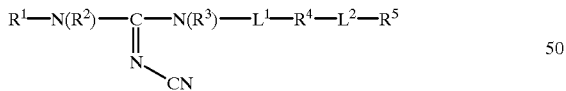

wherein
$R^1$ is 3-pyridyl, 4-pyridyl, or quinolinyl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, alkylcarbonyloxy, alkyloxycarbonyl, alkylcarbonyl, alkylcarbonylamino, aminocarbonyl, alkylsulfonylamino, aminosulfonyl, sulfonic acid, or alkylsulfonyl;

each of $R^2$ and $R^3$, independently, is H, alkyl, alkoxy, hydroxylalkyl, thioalkyl, aminoalkyl, cycloalkyl, heterocycloalkyl, aryl, heteroaryl, alkylcarbonyloxy, alkyloxycarbonyl, alkylcarbonyl, alkylcarbonylamino, or aminocarbonyl;

$L^1$ is —X$^1$—Y$^1$—X$^2$— in which each of $X^1$ and $X^2$, independently, is a bond, or a $C_{1-6}$ alkylene chain optionally containing a double bond or a triple bond and further optionally substituted with alkyl, alkenyl, alkynyl, alkoxy, hydroxyl, halo, carboxyl, amino, nitro, cyano, cycloalkyl, heterocycloalkyl, aryl, heteroaryl, aminosulfonyl, alkylsulfonylamino, alkylcarbonyloxy, alkyloxycarbonyl, alkylcarbonyl, formyl, alkylcarbonylamino, or aminocarbonyl; and $Y^1$ is —O—, —S—, —SO—, —SO$_2$—, —N(R$^a$)—, —CO—, —N(R$^a$)—CO—, —CO—N(R$^a$)—, —N(R$^a$)—CO—CO—, —N(R$^a$)—SO$_2$—, —SO$_2$—N(R$_a$)—, —N(R$^a$)—CO—O—, —O—CO—N(R$^a$)—, —N(R$^a$)—CO—N(R$^b$)—, —N(R$^a$)—CS—N(R$^b$)—CO—, —CO—N(R$^a$)—CS—N(R$^b$)—, —O—CO—, —CO—O—, —O—SO$_2$—, —SO$_2$—O—, —O—S—CO—N(R$^a$)—, —N(R$^a$)—CO—S—O—, —O—CO—O—, —CO—N(R$^a$)—S—CO—N(R$^b$)—, —N(R$^a$)—CO—S—N(R$^b$)—CO—, or a bond; each of R$^a$ and R$^b$, independently, being H, alkyl, alkoxy, hydroxylalkyl, hydroxyl, amino, nitro, cyano, halo, haloalkyl, cycloalkyl, heterocycloalkyl, aryl, heteroaryl, aralkyl, or heteroaralkyl;

$R^4$ is a bond, or cycloalkyl, cycloalkenyl, or aryl, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminioalkyl, nitro, cyano, aryloxy, heteroaryloxy, aralkyloxy, heteroaralkyloxy, alkylcarbonyloxy, alkyloxycarbonyl, alkylcarbonyl, formyl, oxo, alkylcarbonylamino, aminocarbonyl, alkylsulfonylamino, aminosulfonyl, sulfonic acid, or alkylsulfonyl;

$L^2$ is —X$^3$—Y$^2$—X$^4$— in which each of $X^3$ and $X^4$, independently, is a bond, or a $C_{1-6}$ alkylene chain optionally containing a double bond or a triple bond and further optionally substituted with alkyl, alkenyl, alkynyl, alkoxy, hydroxyl, halo, carboxyl, amino, nitro, cyano, cycloalkyl, heterocycloalkyl, aryl, heteroaryl, aminosulfonyl, alkylsulfonylamino, alkylcarbonyloxy, alkyloxycarbonyl, alkylcarbonyl, formyl, alkylcarbonylamino, or aminocarbonyl; and $Y^2$ is —O—, —S—, —SO—, -SO$_2$—, —N(R$^c$)—, —CO—, —N(R$^c$)—CO—, —CO—N(R$^c$)—, —N(R$^c$)—CO—CO—, —N(R$^c$)—SO$_2$—, —SO$_2$—N(R$^c$)—, —N(R$^c$)—CO—O—, —O—CO—N(R$^c$)—, —N(R$^c$)—CO—N(R$^d$)—, —N(R$^c$)—CS—N(R$^d$)—CO—, —CO—N(R$^c$)—CS—N(R$^d$)—, —O—CO—, —CO—O—, —O—SO$_2$—, —SO$_2$—, —O—S—CO—N(R$^c$)—, —N(R$^c$)—CO—S—O—, —O—CO—O—, —CO—N(R$^c$)—S—CO—N(R$^d$)—, —N(R$^c$)—CO—S—N(R$^d$)—CO—, or a bond; each of R$^c$ and R$^d$, independently, being H, alkyl, alkoxy, hydroxylalkyl, hydroxyl, amino, nitro, cyano, halo, haloalkyl, cycloalkyl, heterocycloalkyl, aryl, heteroaryl, aralkyl, or heteroaralkyl; and $R^5$ is a cyclic moiety having 12–20 ring atoms, optionally substituted with alkyl, cycloalkyl, heterocycloalkyl, aryl, heteroaryl, aralkyl, heteroaralkyl, alkoxy, hydroxyl, hydroxylalkyl, carboxyl, halo, haloalkyl, amino, aminoalkyl, nitro, cyano, aryloxy, heteroaryloxy, aralkoxy, heteroaralkoxy, alkylcarbonyloxy, alkyloxycarbonyl, arylcarbonyloxyalkyl, aryloxycarbonylalkyl, alkylcarbonyl, formyl, oxo, aminocarbonyl, alkylcarbonylamino, alkylsulfonylamino, aminosulfonyl, aminocarbonyloxy, or alkyloxycarbonylamino;

provided that when neither one of $Y^1$ and $Y^2$ is a bond, at least one of $X^2$, $R^4$, and $X^3$ is not a bond;

or an N-oxide derivative or a salt thereof.

24. The compound of claim 23, wherein $R^1$ is unsubstituted 4-pyridyl, and each of $R^2$ and $R^3$, independently, is hydrogen.

25. The compound of claim 23, wherein $Y^1$ is —SO—, —$SO_2$—, —$N(R^a)$—CO—CO—, —$N(R^a)$—$SO_2$—, —$SO_2$—$N(R^a)$—, —$N(R^a)$—CO—$N(R^b)$—, —$N(R^a)$—CS—$N(R^b)$—CO—, —CO—$N(R^a)$—CS—$N(R^b)$—, —O—$SO_2$—, —$SO_2$—O—, —CO—$N(R^a)$—S—CO—N$(R^b)$—, —$N(R^a)$—CO—S—$N(R^b)$—CO—, or a bond.

26. The compound of claim 23, wherein $Y^2$ is —SO—, —$SO^2$—, —$N(R^a)$—CO—CO—, —$N(R^a)$—$SO_2$—, —$SO_2$—$N(R^a)$—, —$N(R^a)$—CO—$N(R^b)$—, —$N(R^a)$—CS—$N(R^b)$—CO—, —CO—$N(R^a)$—CS—$N(R^b)$—, —O—$SO_2$—, —$SO_2$—O—, —CO—$N(R^a)$—S—CO—N$(R^b)$—, —$N(R^a)$—CO—S—$N(R^b)$—CO—, or a bond.

27. The compound of claim 23, wherein $R^5$ is optionally substituted with alkyl, aralkyl, alkylcarbonyloxy, alkyloxycarbonyl, alkoxy, amino, halo, or haloalkyl.

28. The compound of claim 27, wherein $R^1$ is unsubstituted 4-pyridyl, each of $R^2$ and $R^3$, independently, is hydrogen.

29. The compound of claim 28, wherein each of $X^1$ and $X^2$, independently, is a bond or a $C_{1-2}$ alkylene chain, and $Y^1$ is a bond.

30. The compound of claim 29, wherein each of $X^3$ and $X^4$, independently, is a bond or a $C_{1-4}$ alkylene chain, and $Y^2$ is —O—, —$N(R^c)$—CO—, —$N(R^c)$—$SO_2$—, —$N(R^c)$—CO—$N(R^d)$—, or a bond.

31. The compound of claim 30, wherein $R^5$ is fluorenyl, dihydrodibenzoazepine, or dibenzocycloheptenyl.

32. The compound of claim 31, wherein $R^4$ is a bond.

33. The compound of claim 32, where the compound is N-(5-(10,11-dihydro-5H-dibenzo[a,d]cyclohepten-5-yloxy)pentyl)-N'-cyano-N"-pyridin-4-yl-guanidine.

34. The compound of claim 28, wherein neither one of $Y^1$ and $Y^2$ is a bond.

35. The compound of claim 34, wherein $X^1$ is a $C_{1-4}$ alkylene chain, $Y^1$ is —O—, —S—, —O—CO—, —$N(R^a)$—, —$N(R^a)$—CO—, or —$N(R^a)$—CO—$N(R^b)$—, in which each of $R^a$ and $R^b$, independently, is alkyl, alkylcarbonyl, aryl, heteroaryl, aralkyl, or heteroaralkyl, and $X^2$ is a bond.

36. The compound of claim 35, wherein $X^3$ is a $C_{1-4}$ alkylene chain, $Y^2$ is —O—, —S—, —O—CO—, —$N(R^c)$—, —$N(R^c)$—CO—, or —$N(R^c)$—CO—$N(R^d)$—, in which each of $R^c$ and $R^d$, independently, is alkyl, alkylcarbonyl, aryl, heteroaryl, aralkyl, or heteroaralkyl, and $X^4$ is a bond or a $C_{1-2}$ alkylene chain optionally substituted with aryl, heteroaryl, aralkyl, or heteroaralkyl.

37. The compound of claim 36, wherein $R^4$ is a bond.

38. The compound of claim 37, wherein $R^5$ is fluorenyl, dihydrodibenzoazepine, or dibenzocycloheptenyl.

39. The compound of claim 38, where the compound is N-{2-[2-(10,11-dihydro-5H-dibenzo[a,d]cyclohepten-5-yloxy)-ethoxy]-ethyl}-N'-cyano-N"-pyridin-4-yl-guanidine or N-[2-(10,11-dihydro-5H-dibenzo[ad]cyclohepten-5-yloxy)-ethyl]-N-[2-(N'-cyano-N"-pyridin-4yl-guanidino)-ethyl]-acetamide.

\* \* \* \* \*